(12) United States Patent
Suzuki et al.

(10) Patent No.: US 8,277,463 B2
(45) Date of Patent: Oct. 2, 2012

(54) MEDICAL DEVICE AND METHOD OF FIXING INTERNAL ORGAN

(75) Inventors: Yutaka Suzuki, Tokyo (JP); Hideaki Matsunami, Akita (JP); Yasunori Kojo, Akita (JP); Yukihiko Sakaguchi, Akita (JP); Masao Ikeda, Akita (JP)

(73) Assignees: Yutaka Suzuki, Tokyo (JP); Sumitomo Bakelite Co., Ltd., Tokyo (JP)

( * ) Notice: Subject to any disclaimer, the term of this patent is extended or adjusted under 35 U.S.C. 154(b) by 872 days.

(21) Appl. No.: 12/225,209

(22) PCT Filed: Feb. 16, 2007

(86) PCT No.: PCT/JP2007/000094
§ 371 (c)(1),
(2), (4) Date: Sep. 16, 2008

(87) PCT Pub. No.: WO2007/129431
PCT Pub. Date: Nov. 15, 2007

(65) Prior Publication Data
US 2009/0062817 A1 Mar. 5, 2009

(30) Foreign Application Priority Data
Apr. 7, 2006 (JP) ................ P2006-106511

(51) Int. Cl.
*A61B 17/10* (2006.01)
(52) U.S. Cl. ........................... 606/139; 606/144

(58) Field of Classification Search ................ 606/130, 606/144, 148, 139, 151, 153–155, 158, 174, 606/177, 228; 604/116
See application file for complete search history.

(56) References Cited

U.S. PATENT DOCUMENTS
5,098,383 A * 3/1992 Hemmy et al. ............. 604/116
2006/0069398 A1 3/2006 Suzuki et al.

FOREIGN PATENT DOCUMENTS
| | | |
|---|---|---|
| JP | 4-226643 | 8/1992 |
| JP | 2003-225240 | 8/2003 |
| JP | 2005-245591 | 9/2005 |
| JP | 2006-25934 | 2/2006 |
| WO | 2004/075761 | 9/2004 |

OTHER PUBLICATIONS
International Search Report.
* cited by examiner

*Primary Examiner* — Corrine M McDermott
*Assistant Examiner* — Gregory Anderson
(74) *Attorney, Agent, or Firm* — Smith, Gambrell & Russell, LLP

(57) ABSTRACT

A medical device (1) includes a main body (2); a first piercing needle (4) provided slidably with respect to the main body (2); a first holding plate (61) adapted to hold the first piercing needle (4) and provided slidably on the main body (2); and a second holding plate (62) adapted to hold a second piercing needle (3) and detachably and movably mounted on the first holding plate (61), wherein the second holding plate (62) is mounted so as to move to the first holding plate (61) in a predetermined direction.

24 Claims, 24 Drawing Sheets

FIG. 1
(a)
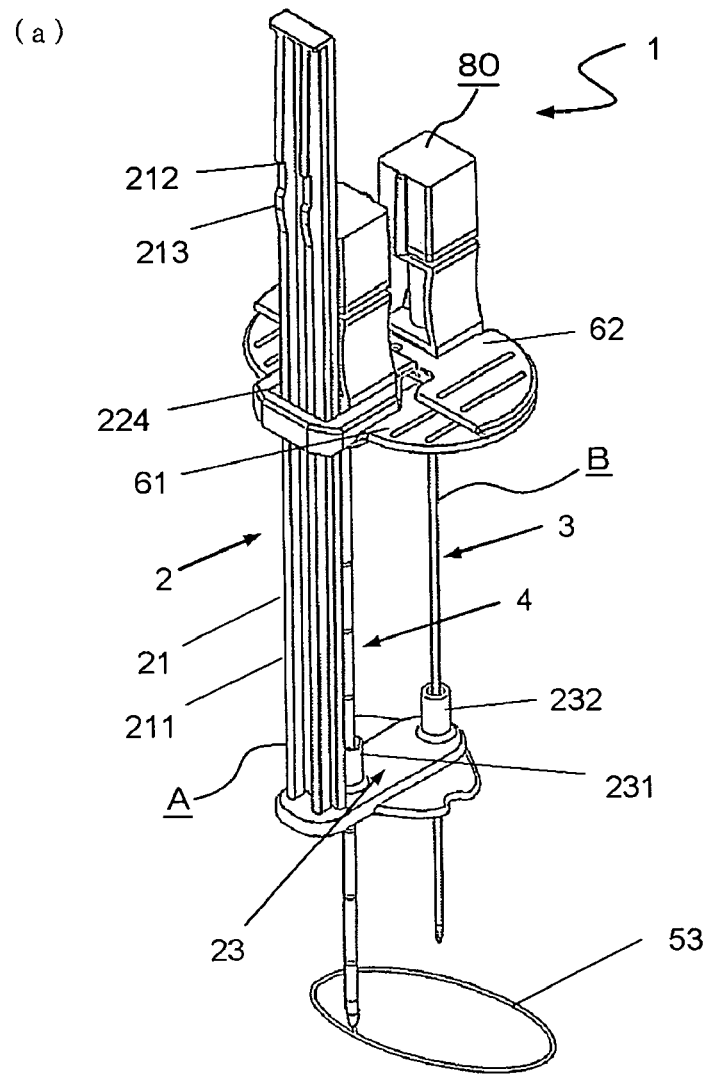
(b)
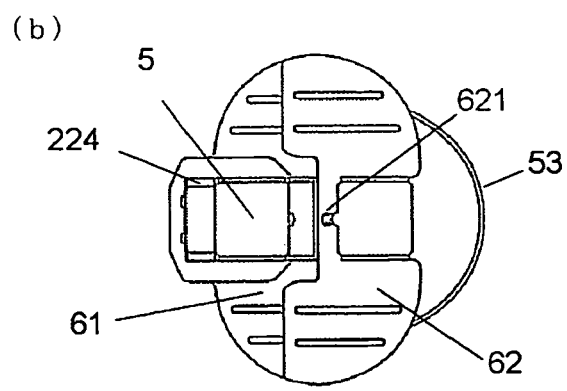

FIG. 3
(a)
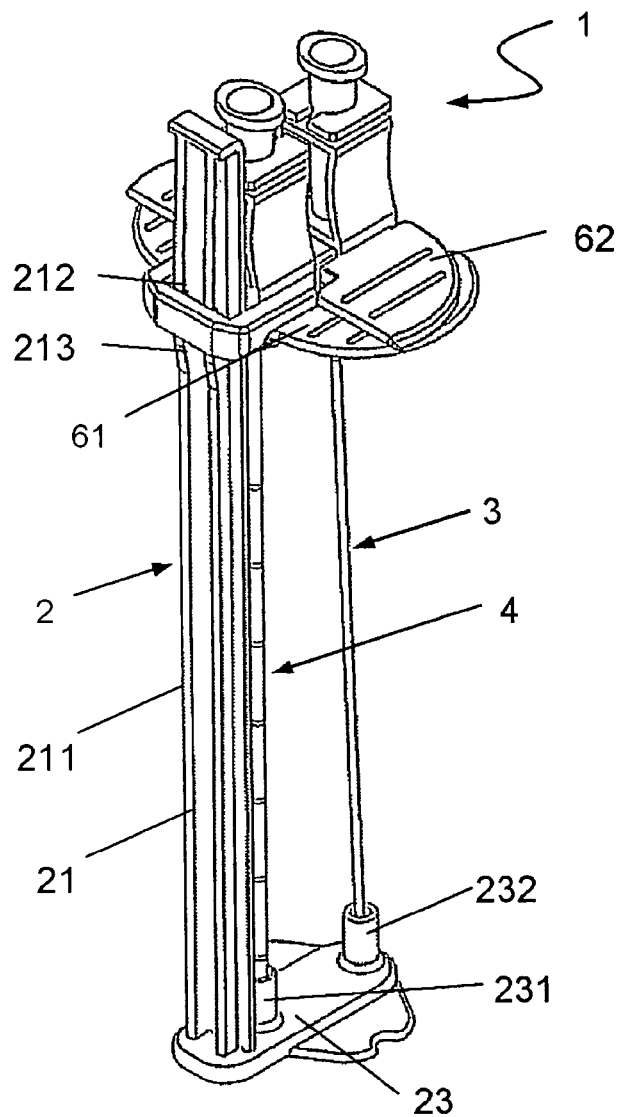
(b)
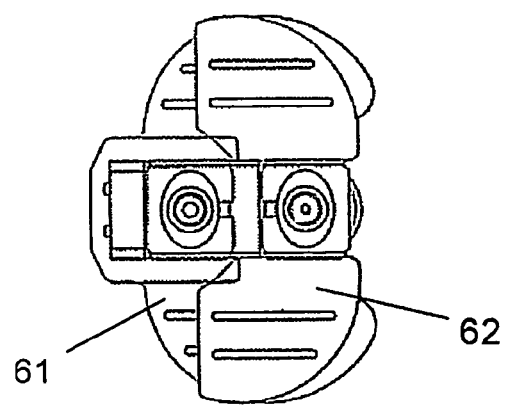

FIG. 5
(a) 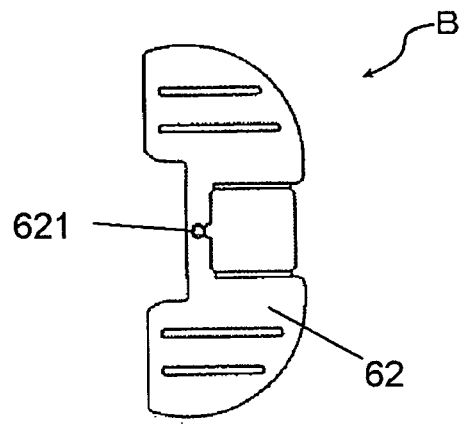
(b) 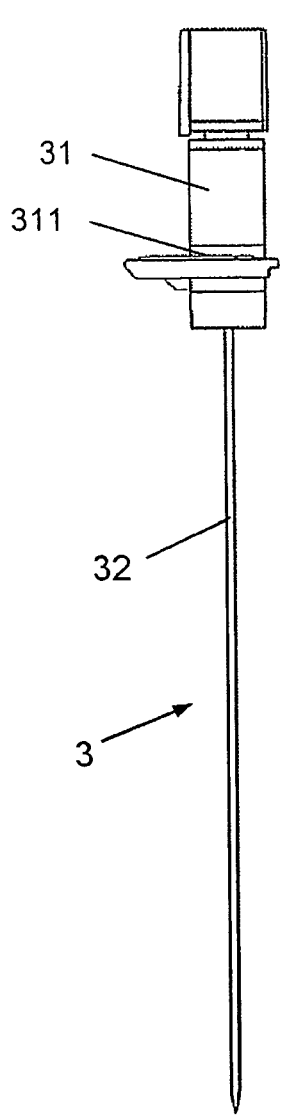
(c) 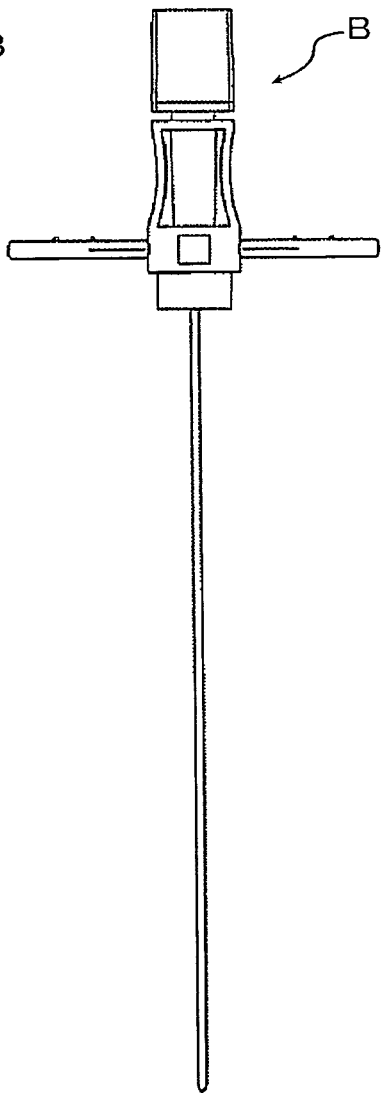

FIG. 18
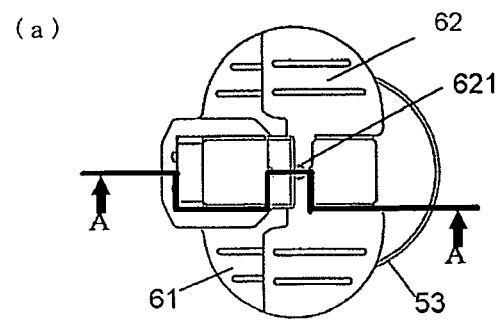
(a)
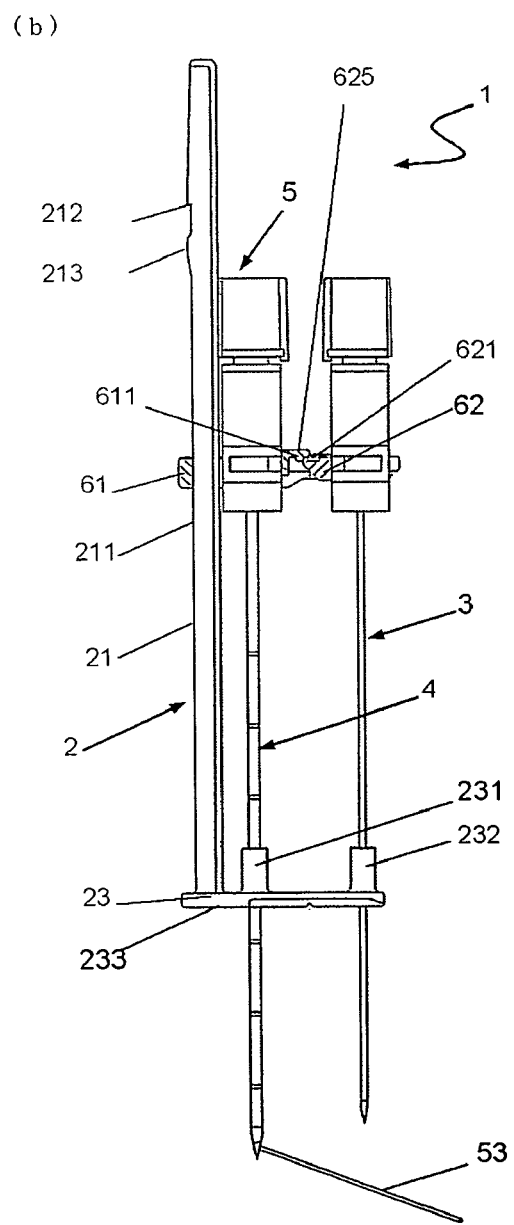
(b)

MEDICAL DEVICE AND METHOD OF FIXING INTERNAL ORGAN

TECHNICAL FIELD

The present invention relates to a medical device used to fix an internal organ of a living body to a body surface of the living body and a method of fixing an internal organ using this medical device.

BACKGROUND ART

There are known three ways of nutrition for a patient unable to take nourishment from a mouth: intravenous feeding, gastric feeding by insertion of a tube from a patient's nose into his or her stomach or the like, and enteral feeding from a gastric fistula.

In recent years, enteral feeding has been frequently managed by means of PEG (percutaneous endoscopic gastrostomy) because of development of enteral nutrition supplements and injection methods therefor.

With the PEG, a through hole penetrating through an abdominal wall and a gastric wall of a patient is formed prior to gastrostomy. Generally, to temporarily fix the mobile gastric wall prior to formation of the through hole, the abdominal wall is secured to the gastric wall by a suture.

As a medical device for such suturing, a medical device or the like configured to include a puncture needle for insertion of a suture ("suture insertion needle"), a puncture needle for grasping the suture ("suture grasping needle") which is arranged in parallel with the suture insertion needle, a stylet slidably inserted into the suture grasping needle, and a fixing member fixing base ends of the suture insertion needle and the suture grasping needle to each other and grasping the suture by the stylet is disclosed (see, for example, Patent Document 1).

Patent Document 1: Japanese Laid-Open Patent Publication No. 04-226643

DISCLOSURE OF THE INVENTION

Problems to be Solved by the Invention

Since the medical device described in the Patent Document 1 is required to simultaneously manipulate the two puncture needles, it is necessary to decide piercing positions of the two puncture needles in advance.

The present invention has been made in the above-stated circumstances. It is an object of the present invention to improve operativity of piercing operation in a medical device for suturing by piercing operation.

Means for Solving the Problems

According to the present invention, there is provided a first medical device including: a first unit including a main body elongated in a vertical direction; a guide unit through which a first guide hole and a second guide hole are penetrated in the vertical direction, the guide unit protruding from a lower end of said main body in a direction orthogonal to said vertical direction; a first puncture needle of a hollow structure supported by said main body near an upper end slidably in the vertical direction, and having a sharp lower end slidably inserted into said first guide hole from above; and a first holding plate integrally fixed to a neighborhood of the upper end of said first puncture needle; and a second unit including a second puncture needle of a hollow structure, having a sharp lower end slidably inserted into said second guide hole from above; and a second holding plate integrally fixed to a neighborhood of an upper end of said second puncture needle, wherein said first unit and said second unit are formed separately to be engageable with and disengageable from each other, and wherein said second holding plate of said second puncture needle inserted into said second guide hole approachably and separably abuts on said first holding plate of said first puncture needle from above.

According to the present invention, there is provided a second medical device including: a main body; a first holding plate provided slidably with respect to said main body; a first puncture needle held by said first holding plate; a second holding plate detachably and movably mounted on said first holding plate; and a second puncture needle held by said second holding plate.

In this medical device, the second holding plate is detachably and movably mounted on the first holding plate. Due to this, the second puncture needle can be detached when the first puncture needle is pierced. Further, after piercing the first puncture needle, the second puncture needle can be attached, and the second holding plate is moved appropriately on the first holding plate to optimally set a piercing position of the second puncture needle. The medical device excellent in operativity is thereby realized.

Furthermore, said second holding plate is restricted from moving to said first holding plate in a predetermined direction, and said first and second puncture needles are mounted so that openings of needlepoints of said first and second puncture needles are opposed to each other. It is thereby possible to easily adjust directions of the needlepoints when the second puncture needle is pierced.

Moreover, an engagement unit engaging said second holding plate with said first holding plate is provided in a state in which said second puncture needle is moved to approach said first puncture needle. In an engagement state, said main body is moved toward the base end side to thereby store the needlepoints of the first and second puncture needles in the storage portion. It is thereby possible to dispose of the puncture needles when the medical device is disposed of.

Furthermore, an attitude of said second puncture needle with respect to said first puncture needle changes to a different attitude by moving said second holding plate toward said first holding plate. It is thereby possible to visually and promptly confirm that the medical device has been used.

According to the present invention, there is provided a first method of fixing an internal organ of a living body to a body surface using the medical device according to the present invention, including: slidably moving said first puncture needle downward with respect to said main body to pierce said first puncture needle from the body surface of said living body into said internal organ, said suture traction tool being inserted into said first puncture needle and said second puncture needle being separated from said first puncture needle; slidably moving said suture traction tool downward within said first puncture needle to protrude said annular portion downward of said second guide hole from a tip end of said first puncture needle; rotating said guide unit as well as said main body around said pierced first puncture needle up to a desired position according to need; inserting said second puncture needle into said second guide hole of said guide unit arranged at the desired position to pierce said second puncture needle into up to an interior of said internal organ, thereby opposing the lower end of said second puncture needle to said annular portion; inserting a suture into said second puncture needle from the upper end of said second puncture needle, and protruding the suture from the lower end of said second puncture needle; slidably moving said suture traction tool upward to cause said annular portion to grasp said suture; and exposing one end of said suture grasped by said annular portion to upward of said body surface, and binding the one end of said suture to other end of said suture.

According to the present invention, there is provided a second method of fixing an internal organ of a living body to a body surface using the medical device according to the present invention, including: slidably moving said first puncture needle downward with respect to said main body to pierce said first puncture needle from the body surface of said living body into said internal organ, said suture traction tool being inserted into said first puncture needle and said second puncture needle being separated from said first puncture needle; slidably moving said suture traction tool downward within said first puncture needle to protrude said annular portion downward of said second guide hole from a tip end of said first puncture needle; inclining said pierced first puncture needle with respect to said body surface at up to a desired angle according to need; inserting said second puncture needle into said second guide hole of said guide unit arranged at a desired position to pierce said second puncture needle into up to an interior of said internal organ, thereby opposing the lower end of said second puncture needle to said annular portion; inserting a suture into said second puncture needle from the upper end of said second puncture needle, and protruding the suture from the lower end of said second puncture needle; slidably moving said suture traction tool upward to cause said annular portion to grasp said suture; and exposing one end of said suture grasped by said annular portion to upward of said body surface, and binding the one end of said suture to other end of said suture.

According to the present invention, there is provided a third method of fixing an internal organ of a living body to a body surface using the medical device according to the present invention, including: slidably moving said first puncture needle downward with respect to said main body to pierce said first puncture needle from the body surface of said living body into said internal organ, said suture traction tool being inserted into said first puncture needle and said second puncture needle being separated from said first puncture needle; slidably moving said suture traction tool downward within said first puncture needle to protrude said annular portion downward of said second guide hole from a tip end of said first puncture needle; rotating said guide unit as well as said main body around said pierced first puncture needle up to a desired position according to need, and inclining said first puncture needle with respect to said body surface at up to a desired angle according to need; inserting said second puncture needle into said second guide hole of said guide unit arranged at the desired position to pierce said second puncture needle into up to an interior of said internal organ, thereby opposing the lower end of said second puncture needle to said annular portion; inserting a suture into said second puncture needle from the upper end of said second puncture needle, and protruding the suture from the lower end of said second puncture needle; slidably moving said suture traction tool upward to cause said annular portion to grasp said suture; and exposing one end of said suture grasped by said annular portion to upward of said body surface, and binding the one end of said suture to other end of said suture.

Although the vertical direction is defined in the present invention, this is defined for the sake of convenience so as to briefly describe the correspondence among the constituent element of the present invention and is not intended to limit the direction during manufacturing or during use if the present invention is carried out.

Although a plurality of steps is described in order in the method of fixing the internal organ according to the present invention, the order is not intended to limit an order of executing a plurality of steps. Due to this, if the method of manufacturing according to the present invention is carried out, the order of the plural steps may be changed within a scope without departure.

Advantage of the Invention

The present invention can provide a medical device used when a body surface part is secured to an internal tissue by a suture and capable of improving operativity of piercing operation.

INDUSTRIAL APPLICABILITY

The present invention relates to a medical device used to secure a body surface part to an internal tissue by a suture. Specifically, the present invention is preferably used to fix an abdominal wall to a gastric wall to facilitate insertion of a catheter during percutaneous endoscopic gastrostomy (PEG) performed for supply of nutrition supplements, discharge of body fluids or the like.

BRIEF DESCRIPTION OF THE DRAWINGS

The above-described objects and other objects, characteristics, and advantages will be more apparent with reference to preferred embodiments described below and accompanied drawings.

FIGS. 1(a) and 1(b) are a perspective view and a top view showing an example of a medical device according to the present invention, respectively.

FIGS. 3(a) and 3(b) are a perspective view and a top view if needlepoints of puncture needles of the medical device are stored in a main body, respectively.

FIGS. 5(a), 5(b), and 5(c) are a top view, a front view, and a right side view if a suture insertion needle is fitted into a second holding plate, respectively.

FIGS. 18(a) and 18(b) are a top view and a cross-sectional view showing a restriction unit restricting movement in a sliding direction, respectively.

BEST MODE FOR CARRYING OUT THE INVENTION

Figure 2:
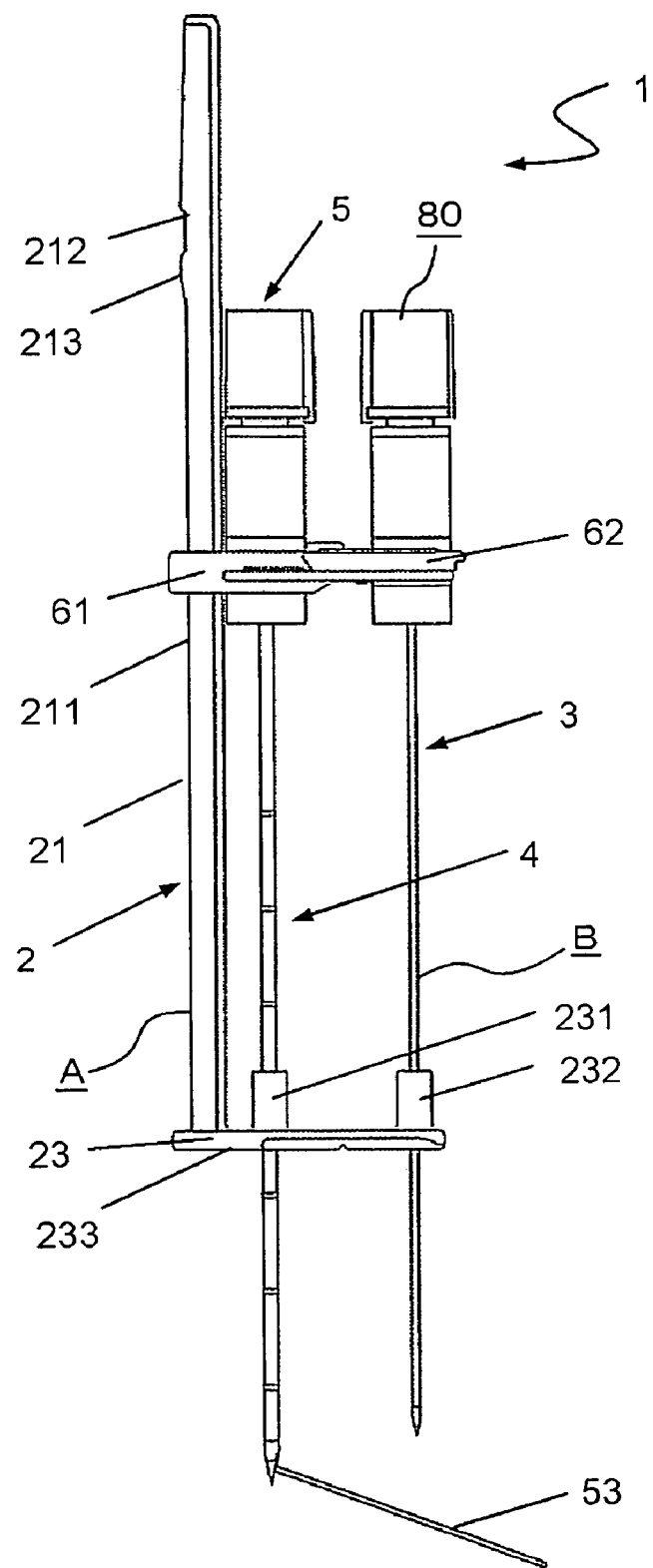
FIG. 2 is a front view of the medical device.

Preferred embodiments of the present invention will be described hereinafter with reference to the drawings while referring to examples of a medical device used if a body surface part is secured to an internal tissue by a suture.

Common constituent elements are denoted by the same reference symbols in all drawings and will not be repeated in the following description. Furthermore, in the drawings, an upper side is assumed as a base (proximal) end side and a lower side is assumed as a tip end side. FIG. 1(a) is a perspective view showing one embodiment of a medical device according to the present invention and FIG. 1(b) is a top view thereof.

As shown in FIGS. 1 to 5, a medical device 1 according to the embodiment includes a first unit A and a second unit B, and the first unit A and the second unit B are formed separately to be engageable with and disengageable from each other.

Figure 4:
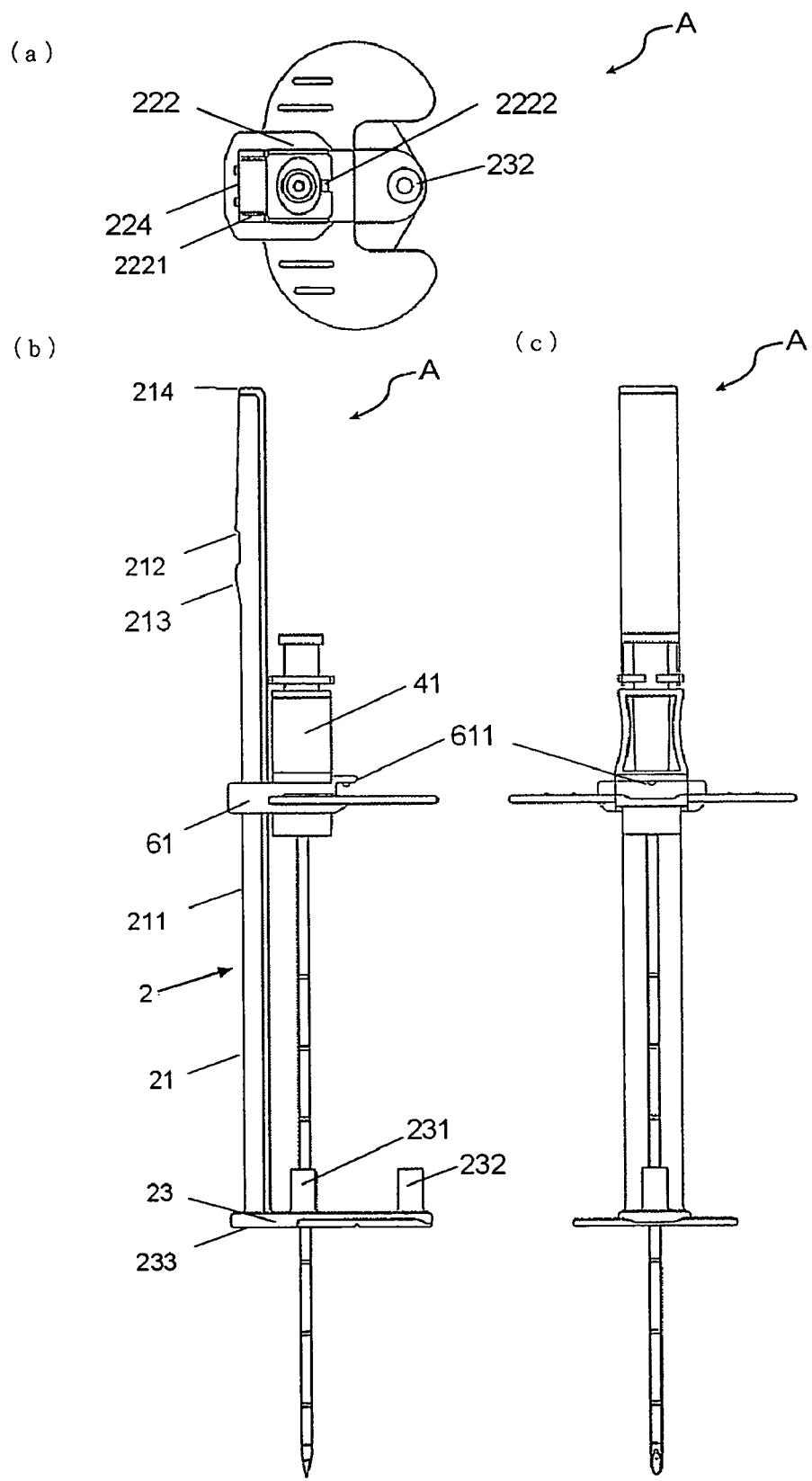
FIGS. 4(a), 4(b), and 4(c) are a top view, a front view and a right side view if the main body, a suture grasping needle (first puncture needle), and a first holding plate are assembled together, respectively.

As shown in FIG. 4, the first unit A includes a main body 2 elongated in a vertical direction, a storage unit 23 through which a first guide hole and a second guide hole are penetrated in the vertical direction, protruding from a lower end of the main body 2 in a direction orthogonal to the vertical direction, and serving as a guide unit, a first puncture needle 4 of a hollow structure vertically slidably supported by the main body 2 near an upper end thereof and having a sharp-pointed lower end slidably inserted into the first guide hole from above, and a first holding plate 61 integrally fixed to neighborhoods of the upper end of the first puncture needle 4.

As shown in FIG. 5, the second unit B includes a second puncture needle 3 of a hollow structure having a sharp-pointed lower end slidably inserted into the second guide hole from above, and a second holding plate 62 integrally fixed to neighborhoods of an upper end of the second puncture needle 3.

Figure 9:
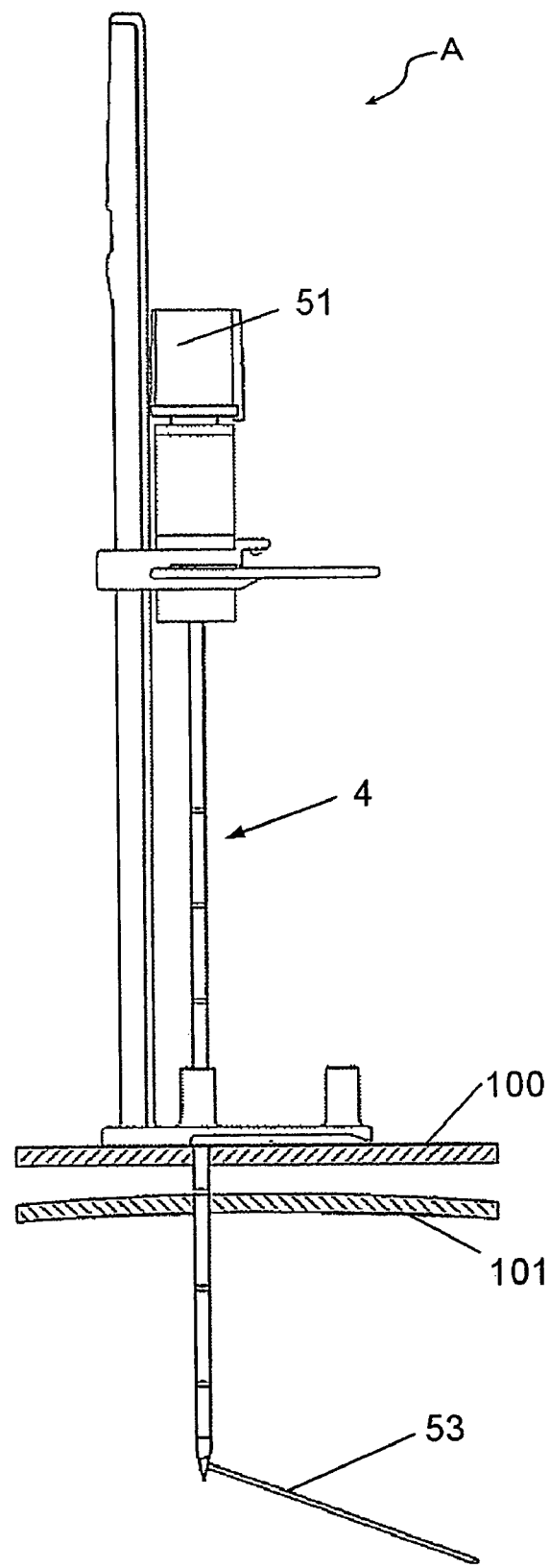
FIG. 9 is a front view showing a state of protruding an annular portion of the suture traction tool from the needlepoint of the suture grasping needle.
Figure 10:
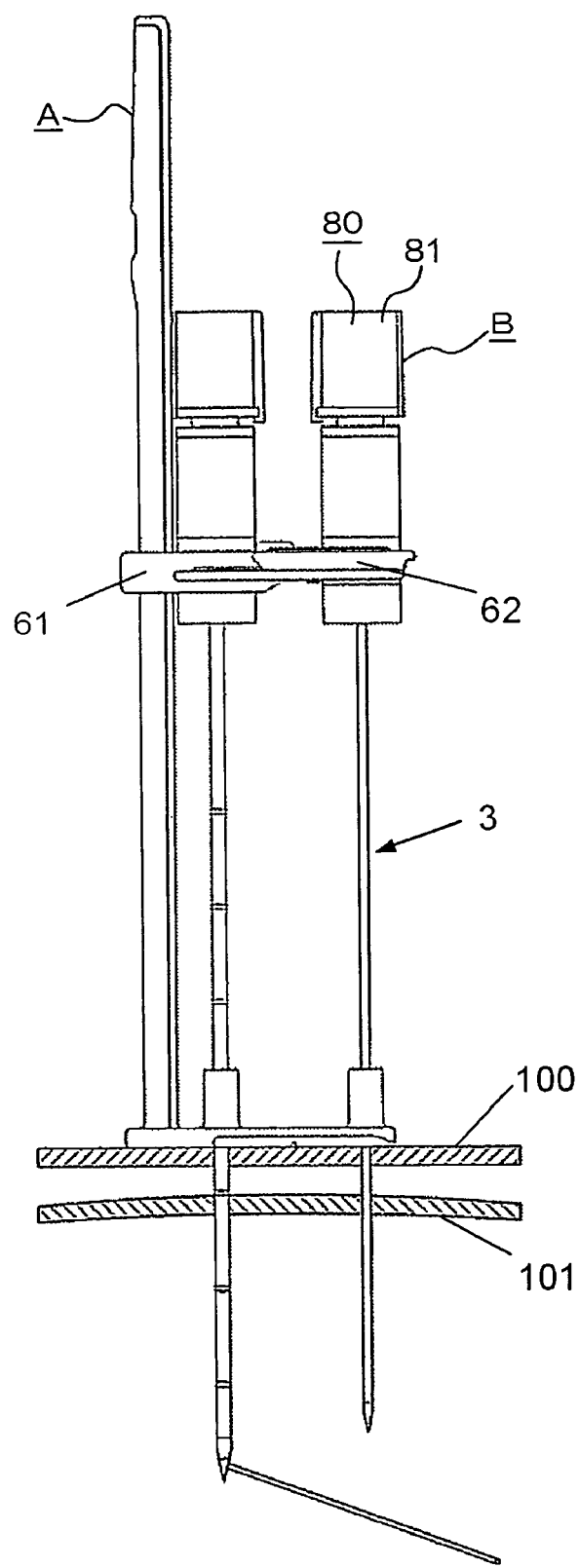
FIG. 10 is a front view showing a state of piercing the suture insertion needle.

As shown in FIGS. 9 and 10, in the medical device 1 according to the embodiment, which will be described in detail later, the second holding plate 62 of the second puncture needle 3 inserted into the second guide hole abuts on the first holding plate 61 of the first puncture needle 4 from above to be freely approachable to or separable from the first holding plate 61.

Figure 15:
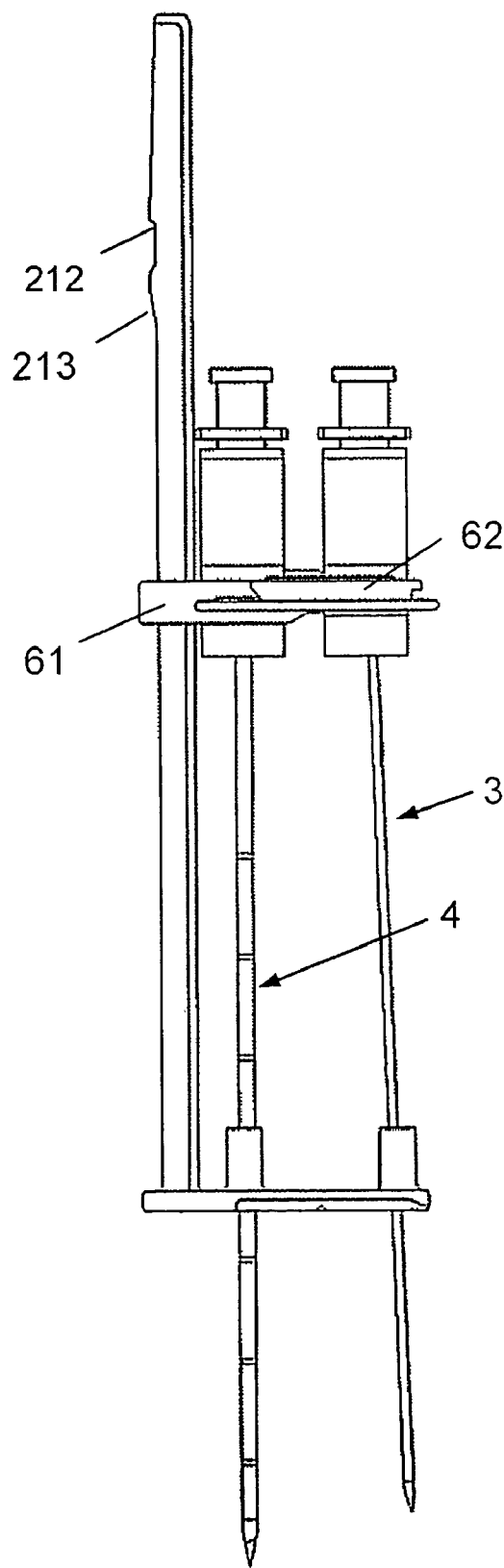
FIG. 15 is a front view showing a state of sliding the second holding plate of the pulled-out medical device toward the first holding plate and fitting the second holding plate into the first holding plate.
Figure 16:
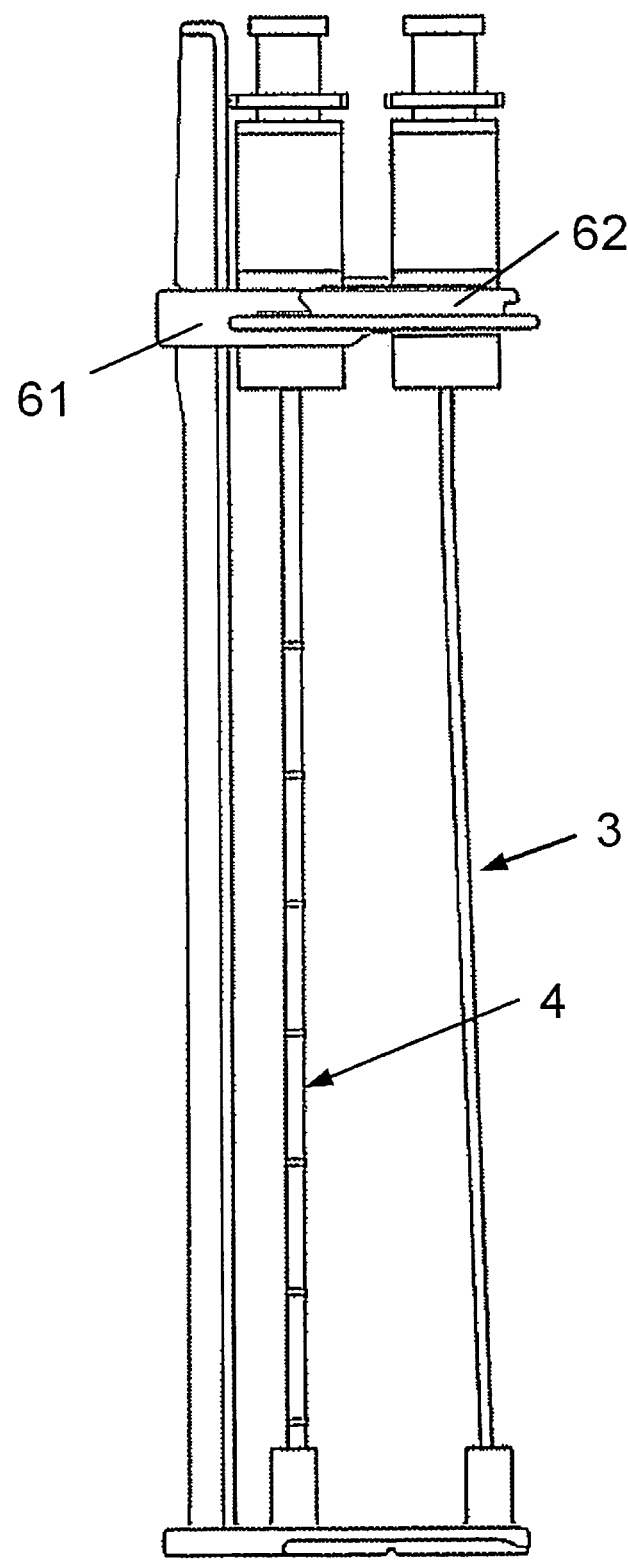
FIG. 16 is a front view showing a state of storing the needlepoints of the puncture needles of the medical device in the main body.

The first holding plate 61 and the second holding plate 62 include a convex portion 611 and a concave portion 621 serving as connectors connected to each other to be freely approachable to or separable from each other, respectively. In a state in which the first holding plate 61 and the second holding plate 62 are connected to each other by the convex portion 611 and the concave portion 621, an upper end distance between the first puncture needle 4 and the second puncture needle 3 is smaller than a distance between the first and second guide holes as shown in FIGS. 15 and 16.

It is to be noted that the first holding plate 61 is connected to the second holding plate 62 by the convex portion 611 and the concave portion 621 in a direction orthogonal to the vertical direction. In a state in which the first holding plate 61 and the second holding plate 62 the convex portion 611 and the concave portion 621 of which are disconnected are engaged with each other, the upper end distance between the first puncture needle 4 and the second puncture needle 3 is larger than the distance between the first and second guide holes.

In the storage unit 23, a cylindrical first storage portion 231 in which the first guide hole is formed and a cylindrical second storage portion 232 in which the second guide hole is formed are formed. The main body 2 includes a locking part 212 locking the first puncture needle 4 in a state in which a needlepoint of the first puncture needle 4 is stored in the first storage portion 231, and a needlepoint of the second puncture needle 3 connected to this locked first puncture needle 4 by the convex portion 611 and the concave portion 621 is stored in the second storage portion 232.

In the first holding plate 61, a slide hole 224 in which the main body 2 is slidably located is formed. The locking part 212 is formed in the main body 2 as a concave portion with which the first holding plate 61 sliding in the slide hole 224 is disengageably engaged.

Figure 7:
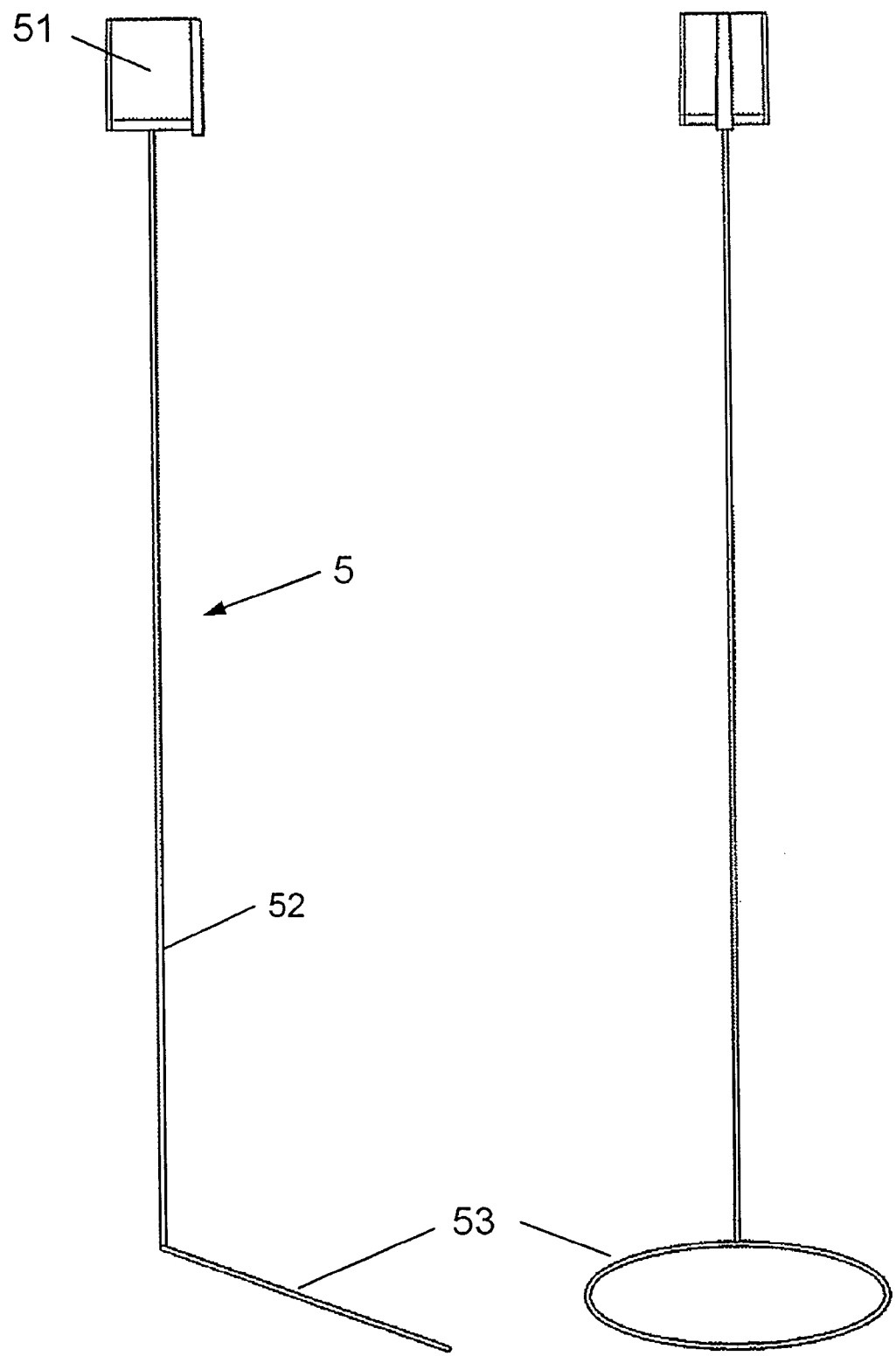
FIG. 7 is a front view and a right side view of a suture traction tool.

As shown in FIG. 7, the medical device 1 according to the embodiment also includes a suture traction tool 5. This suture traction tool 5 includes a rod portion 52 slidably arranged in the first puncture needle 4, a handle portion 51 formed integrally with an upper end of the rod portion and located above an upper end of the first puncture needle 4, and an annular portion 53 serving as a snare formed integrally with a lower end of the rod portion 52 and protruding or retreating from a lower end of the first puncture needle 4.

The first puncture needle 4 is formed as a so-called Huber needle and an opening of the needlepoint thereof is formed on a side opposed to the second puncture needle 3. The suture traction tool 5 is rotatable in a state of being inserted into the first puncture needle 4.

However, in the suture traction tool 5, the handle portion 51 is formed to have a structure of being engaged with the upper end of the first puncture needle 4 while the annular portion 53 protrudes in an appropriate direction from the opening of the needlepoint of the first puncture needle 4 that is the Huber needle.

On the other hand, the second puncture needle 3 is formed as an ordinary hollow needle having the needlepoint formed to have an inclined surface. An internal needle 80 is detachably inserted into the second puncture needle 3. This internal needle 80 may include, for example, a rod portion (not shown) communicating with the suture insertion needle 3 from an upper end to a lower end of an interior of the suture insertion needle 3 and a handle portion 81 connected to an upper end of the needle part.

Further, this internal needle 80 has an inclined surface corresponding to the second puncture needle 3 on a needlepoint thereof. The internal needle 80 is also rotatable in a state of being inserted into the second puncture needle 3. However, the handle portion 81 is formed to have a structure of being engaged with the upper end of the second puncture needle 3 in a predetermined direction. In this way, in a state in which the handle portion 81 is appropriately engaged, an inclined surface of the needlepoint of the second puncture needle 3 is flush with the inclined surface of the needlepoint of the internal needle 80.

More specifically, the medical device 1 includes the main body 2, the first holding plate 61 provided slidably on the main body 2, and the first puncture needle 4 held by the first holding plate 61. The second holding plate 62 is mounted on the first holding plate 61.

The second holding plate 62 is provided detachably from the first holding plate 61. Further, the second holding plate 62 is provided to be freely movable in a predetermined region on the first holding plate 61.

The second holding plate 62 is restricted from moving to the first holding plate 61 in a predetermined direction, thereby keeping an attitude of opposing opening portions of needlepoints of the first and second puncture needles 4 and 3 to each other (FIG. 1(*b*)).

Furthermore, engagement units 611 and 621 are provided on the first holding plate 61 and the second holding plate 62 (FIGS. 4(*b*) and 5(*a*)), respectively so that the second holding plate 62 is engaged with the first holding plate 61 by moving the second holding plate 62. By moving the second holding plate 62 to the first holding plate 61, an attitude of the second puncture needle 3 changes from an initial attitude.

Moreover, storage portions 231 and 232 storing the needlepoints of the first and second puncture needles 3 and 4 are provided on a tip end side of the main body 2 (FIG. 1(*a*)). The first holding plate 61 includes a restriction unit 625 restricting movement of the second holding plate 62 in a sliding direction. The restriction unit 625 causes a part of the first holding plate 61 to project to cover up a part of the second holding plate 62 (FIGS. 18(*a*) and 18(*b*)).

If the first holding plate 61 is engaged with the second holding plate 62 and caused to slide toward a base end of the main body 2, the needlepoints of the first and second puncture needles 3 and 4 are stored in the storage portions 231 and 232, respectively.

The main body 2 includes the locking part 212 on the base end thereof, and the first and second puncture needles 3 and 4 are stored in the storage portions 231 and 232 at a position at which the first holding plate 61 is locked, respectively (FIGS. 3(*a*) and 3(*b*)).

Figure 17:
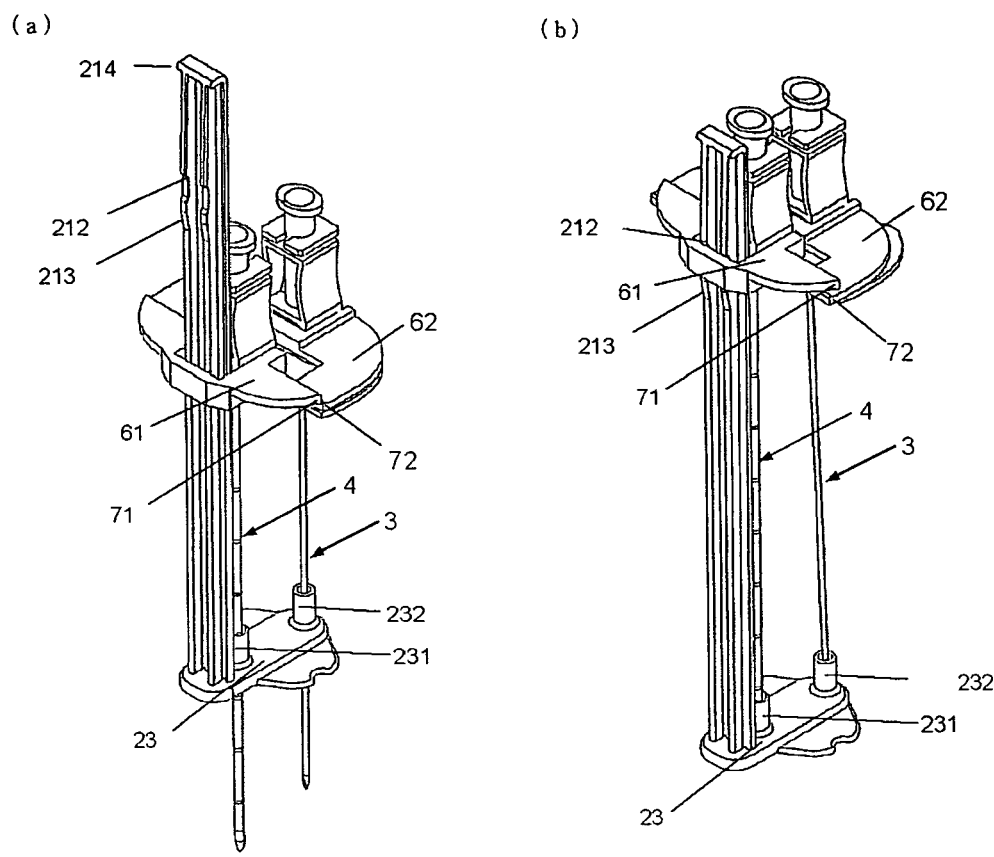
FIGS. 17(a) and 17(b) are perspective views showing a state of pulling out a main body from a patient and a state of storing needlepoints of puncture needles in a main body according to another embodiment, respectively.

Alternatively, the engagement units 611 and 621 may be constituted by a concave portion provided in one of the first holding plate 61 and the second holding plate 62 and a convex portion provided in the other holding plate or may be claws provided on the first holding plate 61 and the second holding plate 62, respectively (FIGS. 17(*a*) and 17(*b*)).

Configurations of the respective elements of the medical device will be described.

As shown in FIG. 2, the main body 2 supports the first holding plate 61. The suture grasping needle 4 is slidable with respect to the main body 2. The main body 2 includes a support member 21 and the storage unit 23 provided on a tip end of the support member 21 and storing the needlepoints of the puncture needles. The storage unit 23 functions to store sharp needlepoints of the two puncture needles, that is, the suture grasping needle 4 that is the first puncture needle and the suture insertion needle 3 that is the second puncture needle.

The support member 21 supports the holding plate 61 that is a slidable plate. The first holding plate 61 holds the suture grasping needle 4, and the slide hole 224 into which the support member 21 is inserted is provided in the first holding plate 61. Due to this, the first holding plate 61 is slidable with respect to the main body 2. A range in which the first holding plate 61 is slidable with respect to the main body 2 corresponds to a slide unit 211.

The first holding plate 61 slides on the slide unit 211, whereby the first holding plate 61 freely moves forward and backward with respect to the support member 21, and a length of the suture grasping needle 4 by which the suture grasping needle 4 is pierced through a tissue can be adjusted to facilitate piercing.

Moreover, if the second holding plate 62 is mounted on the first holding plate 61, the suture insertion needle 3 can be pierced so as to always maintain the positional relationship between the needlepoint of the suture insertion needle 3 and the needlepoint of the suture grasping needle 4.

The locking part 212 engaged with the sliding first holding plate 61 is provided on a base end of the slide unit 211.

The locking part 212 is arranged on the support member 21 in a positional relationship that the sharp needlepoint of the suture insertion needle 3 and the sharp needlepoint of the suture grasping needle 4 are stored in the second storage portion 232 and the first storage portion 231 of the storage unit 23, respectively when the slide hole 224 of the first holding plate 61 is fitted into the locking part 212.

This can maintain a state of storing the sharp needlepoints when the medical device is disposed of after being used and can reduce secondary accidents of erroneous piercing of the needles into healthcare professionals. Moreover, the needlepoints of the two puncture needles are stored in the respective storage portions in a state in which the second holding plate 62 slides toward and is fitted into the first holding plate 61. Due to this, the suture insertion needle 4 widens toward the end with respect to the support member 21 and the suture grasping needle 4, thereby making it possible to promptly and visually recognize that the suture insertion needle 4 is used.

Preferably, a guide surface 213 may be provided on the tip end side relative to the locking part 212. The guide surface 213 is provided on the tip end side relative to the locking part 212 on the base end of the slide unit 211, and a slide surface of the slide unit 211 is formed so that a diameter thereof is larger toward the locking part 212 and smaller thereafter.

During ordinary use, the first holding plate 61 slides on the slide unit 211 of the support member 21 on the tip end side relative to the guide surface 213. During disposal time, the holding plate 61 overrides the guide surface 213 and is fitted into the locking part 212, and the state is changed over to a state in which the sharp needlepoints of the suture insertion needle 3 and the suture grasping needle 4 are stored. It is thereby possible to hold the changeover to a needlepoint storage state.

As shown in FIGS. 4(*a*) and 4(*b*), it is further preferable to provide an operating unit 214 on the base end of the support member 21. By providing the operating unit 214, a changeover operation of causing the first holding plate 61 to override the guide surface 213 and changing over to the needlepoint storage state can be easily carried out only by an operation of pressing down the operating unit 214 while supporting the tip end of the first holding plate 61 by the hand.

The storage unit 23 functions to store the needlepoints of the puncture needles and, at the same time, to improve stability during use of the medical device 1 by abutting on the body surface part for a procedure. As shown in FIGS. 1, 2, and 3, the storage unit 23 is flat and includes, on a base end surface thereof, the second storage portion 232 including an internal cavity in which the suture insertion needle 3 can be stored and the first storage portion 231 including an internal cavity in which the suture grasping needle 4 can be stored.

The second storage portion 232 functions to not only store the needlepoint but also improve stability during piercing of the suture insertion needle 3. After piercing the suture grasping needle 4 into a tissue, a medical doctor can decide a position at which the suture insertion needle 3 is pierced.

After the piercing position of the suture insertion needle 3 is determined, the support member 21 of the main body 2 is rotated about the suture grasping needle 4, thereby positioning the second storage portion 232 at the piercing position. Furthermore, while the positional relationship that the needlepoint of the suture insertion needle 3 is inserted into the internal cavity of the second storage portion 232 is maintained, the second holding plate 62 is mounted on the first holding plate 61.

The direction of the opening on the needlepoint of the suture insertion needle 3 is decided when the second holding plate 62 is mounted on the first holding plate 61. It is, therefore, preferable to shape the first holding plate 61 and the second holding plate 62 so as to be able to visually determine that the second holding plate 62 is always mounted on the first holding plate 61 in the same direction at a glance. It is also preferable to shape the first holding plate 61 so as to be able to easily check the second storage portion 232 during piercing of the suture insertion needle 3.

The first and second holding plates include fitting units that enable the first and second holding plates to be fitted into each other by sliding the second holding plate toward the first holding plate. FIG. 3 shows a fitting state. Each of the fitting unit is not limited to a specific one. However, it is preferable that the convex portion 611 is provided in the first holding plate 61 as shown in FIG. 4(b) and that the concave portion 621 is provided in the second holding plate 62 as shown in FIG. 5(a). When the second holding plate 62 is caused to slide toward the first holding plate 61, the convex portion 611 is fitted into the concave portion 621 to fit the first holding plate into the second holding plate.

The concave portion 621 may not be provided in the second holding plate 62 if the first holding plate 61 is not detached from the second holding plate 62 at the time of storing the tip ends of the puncture needles in the storage portion. It is preferable to fit the first holding plate into the second holding plate by the fitting units. However, as shown in FIGS. 17(a) and 17(b), the first holding plate 61 may be engaged with the second holding plate 62 by providing first and second claws 71 and 72 as engagement units, respectively without fitting the first holding plate into the second holding plate.

A second hole 2221 into which the suture grasping needle 4 can be inserted is provided in a fixed unit 222 (FIG. 4). Furthermore, a flange fitting unit 2222 fitted into a second flange 411 (FIG. 6) of a second hub 41 of the suture grasping needle 4, to be described later, is formed on one surface of the second hole 2221 of the first holding plate (FIG. 4(a)).

By doing so, the suture grasping needle 4 is fitted into the main body 2 only in one direction when the first holding plate 61 is attached to the suture grasping needle 4. Moreover, in a state in which the flange fitting unit 2222 is fitted into the second flange 411, the suture grasping needle 4 neither rotates nor vertically moves about or with respect to the first holding plate 61.

The suture insertion needle 3 functions to insert a suture into an internal tissue.

As shown in FIGS. 5(a), 5(b), and 5(c), the suture insertion needle 3 includes, on a base end thereof, a first hub 31 and a first needle part 32 provided on the needlepoint thereof. Each of the first hub 31 and the first needle part 32 includes an internal cavity, which cavity is used as a passage of the suture.

Further, a first flange 311 is provided on the first hub 31 and fitted into the second holding plate 62.

As already described, the shape of the second holding plate 62 is not limited to a specific one as long as the second holding plate 62 can hold the suture insertion needle 3 and can be mounted on the first holding plate 61. However, it is preferable that the shape is such that a direction of mounting on the first holding plate 61 can be visually determined at a glance.

A material constituting the first holding plate 61, the second holding plate 62, the support member 21, and the storage unit 23 is not limited to a specific material. Examples of the material include vinyl chloride resin, polycarbonate resin, ABS resin, polyacetal resin, polyamide resin, polypropylene resin, polyethylene resin and the like, and metals such as stainless steel. The first holding plate 61, the second holding plate 62, the support member 21, and the storage unit 23 are formed by injection molding or metal working.

The support member 21 may be either formed integrally with or divided from the storage unit 23. Since the storage unit 23 is disposed on a region such as the body surface part of an abdominal part having a small incision by a scalpel, the storage unit 23 is preferably made of a highly transparent resin material. The second holding plate 62 may be formed integrally with the first hub 31.

The suture grasping needle 4 held by the first holding plate 61 slidable on the support member 21 of the main body 2 is set almost parallel to the suture insertion needle 3 by mounting the second holding plate 62 holding the suture insertion needle 3 on the first holding plate 61 through the second storage portion 232 for the suture insertion needle 3. By mounting the second holding plate 62 at an intended position, opening surfaces of the tip ends are almost opposed to each other.

By doing so, if the suture traction tool 5, to be described later, pulls the suture up to the outside of the body through the two puncture needles, a portion in which the suture contacts with the puncture needles while being bent can be limited only to the base ends of the opening surfaces and the base ends of the opening surfaces can be rounded without giving no influence on piercing performances of the puncture needles. Therefore, pulling-up of the suture can be executed smoothly.

The first needle part 32 includes an opening communicating with the internal cavity on a tip end thereof.

The first needle part 32 keeps a constant outside diameter from a base end to near the tip end, and a sharp tip end is formed ahead of the constant outside diameter portion. Although a shape of the tip end is not limited to a specific one, it is preferably a Huber shape excellent in straightness.

The outside diameter of the first needle part 32 is not limited to a specific one. Generally, it suffices that the first needle part 32 is a puncture needle having an inside diameter at which a 2-0 (0.29 mm) suture and a 3-0 (0.24 mm) suture often used for suturing and fixing can be inserted. The outside diameter is preferably that of a gauge number not less than 15 G and not more than 25 G, more preferably that of a gauge number not less than 19 G and not more than 21 G.

If the outside diameter falls within the above-stated range, a piercing resistance of the suture insertion needle 3 can be reduced, thus facilitating piercing the needle 3 into the body. It is to be noted that G is a symbol normally representing an outside diameter of a needle. For example, an outside diameter of the 12 G needle is an outside diameter when a sum of diameters of 12 needles corresponds to one inch (about 2.5 centimeters).

Although an entire length of the first needle part 32 is not limited to a specific one, it is preferably equal to or larger than 20 mm and equal to or smaller than 200 mm, more preferably equal to or larger than 80 mm and equal to or smaller than 100 mm. If the entire length falls within the above-stated range, the tip end of the puncture needle can reach an interior of an internal organ of a patient and stability of the main body including the puncture needle after piercing can be improved.

The suture grasping needle 4 functions to insert the suture traction tool into an internal tissue. The suture grasping needle 4 can also insert a storage wire, whereby the body surface part can be secured to the internal tissue by the suture and the storage wire can be inserted into the living body. A position at which the storage wire is inserted can act as a catheter insertion position.

Figure 6:
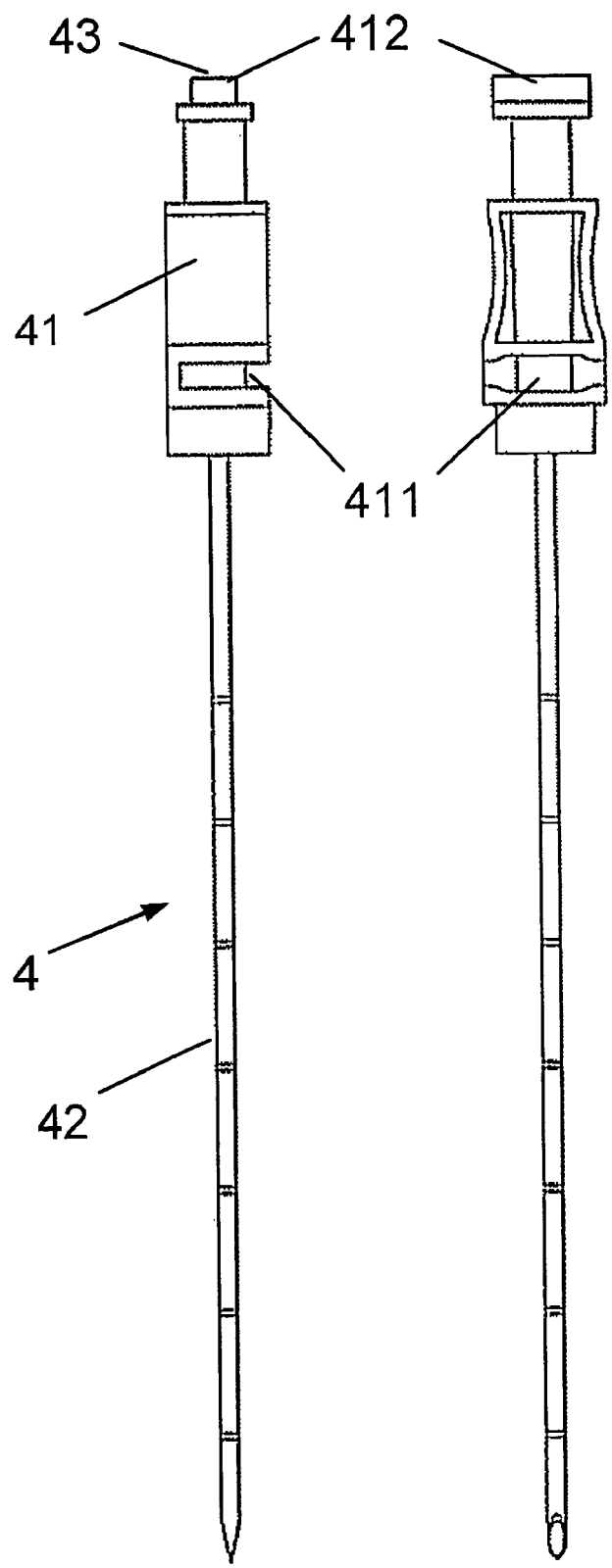
FIG. 6 is a front view and a right side view of the suture grasping needle.

As shown in FIG. 6, the suture grasping needle 4 includes the second hub 41 on the base end and a second needle part 42 provided on the tip end.

Each of the second hub 41 and the second needle part 42 includes an internal cavity 43, which cavity is used as a passage of the suture traction tool. The internal cavity 43 can be also used as a passage of the storage wire to be described later.

Moreover, the second flange 411 fitted into the flange fitting unit 2222 of the first holding plate 61 is formed on the second hub 41. This enables the suture grasping needle 4 to be fitted into the first holding plate 61 only in one direction. Further, in a state in which the second flange 411 is fitted into the flange fitting unit 2222, the suture grasping needle 4 neither rotates nor vertically moves about or with respect to the first holding plate 61.

The second needle part 42 includes an opening communicating with the internal cavity 43 on a tip end thereof.

The second needle part 42 keeps a constant outside diameter from a base end to near the tip end, and a sharp tip end is formed ahead of the constant outside diameter portion. Although a shape of the tip end is not limited to a specific one, it is preferably a Huber shape excellent in straightness.

The outside diameter of the second needle part 42 is not limited to a specific one. Generally, a 2-0 (0.29 mm) suture and a 3-0 (0.24 mm) suture are often used for the suture grasping needle according to the embodiment while being folded back. Due to this, it suffices that the puncture needle has an inside diameter at which the two sutures can be inserted. The outside diameter is preferably that of a gauge number not less than 12 G and not more than 22 G, more preferably that of a gauge number not less than 17 G and not more than 21 G. If the outside diameter falls within the above-stated range, a piercing resistance of the suture grasping needle 4 can be reduced, thus facilitating piercing the needle 4 into the body.

Although an entire length of the second needle part 42 is not limited to a specific one, it is preferably equal to or larger than 20 mm and equal to or smaller than 200 mm, more preferably equal to or larger than 80 mm and equal to or smaller than 100 mm. If the entire length falls within the above-stated range, the tip end of the puncture needle can reach the interior of the internal organ of the patient and stability of the main body including the puncture needle after piercing can be improved.

If the storage wire is to be inserted into the internal cavity 43, an outside diameter of the storage wire to be inserted is not limited to a specific one. The outside diameter is preferably equal to or larger than 0.1 mm and equal to or smaller than 1.5 mm, more preferably equal to or larger than 0.7 mm and equal to or smaller than 1.1 mm. It is necessary to select the suture grasping needle 4 according to each outside diameter of the storage wire to be inserted. It is possible to not only secure the body surface part to the internal tissue by the suture but also insert the storage wire into the living body.

The suture traction tool 5 is inserted into the suture grasping needle 4, and functions to grasp the suture inserted from the suture insertion needle 3 in the internal tissue and to tract the suture up to the body surface part. This can facilitate securing the body surface part to the internal tissue by the suture.

As shown in FIG. 7, the suture traction tool 5 includes the rod portion 52, the handle portion 51 formed on the base end of the rod portion 52, and the annular portion 52 on the tip end side. This annular portion 53, which is formed out of a highly elastic wire rod, can slidably move in the first puncture needle 4 while being compressed into a linear state, and enlarges annularly when protruding from the lower end of the first puncture needle 4.

The handle portion 51 is a generally rectangular parallelepiped and an internal surface of the handle portion 51 is bored into a generally cylindrical shape. The internal surface is preferably bored into an elliptic shape. Further, by forming a base end 412 of the second hub 41 of the suture grasping needle 4 into an elliptic shape, an opening direction of the annular portion 53 of the suture traction tool 5 protruding from the sharp needlepoint of the suture grasping needle 4 can be limited to two directions.

More preferably, a mark may be formed in a direction in which the annular portion 53, to be described later, protrudes with respect to the suture traction tool 5, thereby making it possible to facilitate recognizing which direction the annular portion 53 faces.

A material constituting the handle portion 51 is not limited to a specific one. Examples of the material include vinyl chloride resin, polycarbonate resin, ABS resin, polyacetal resin, polyamide resin, polypropylene resin, polyethylene resin and the like, and metals such as stainless steel. The handle portion 51 is formed by injection molding or metal working.

An outside diameter of the rod portion 52 is smaller than the inside diameter of the suture grasping needle 4.

Although the outside diameter of the rod portion 52 is not limited to a specific one, it is preferably equal to or larger than 0.3 mm and equal to or smaller than 0.8 mm, more preferably equal to or larger than 0.4 mm and equal to or smaller than 0.7 mm. If the outside diameter is within the above-stated range, the rod portion 52 of the suture traction tool 5 can be inserted into the internal cavity 43 of the suture grasping needle 4.

Although a length of the rod portion 52 is not limited to a specific one, it is preferably equal to or larger than 45 mm and equal to or smaller than 225 mm if the entire length of the second needle part 42 of the suture grasping needle 4 is equal to or larger than 20 mm and equal to or smaller than 200 mm, more preferably equal to or larger than 105 mm and equal to or smaller than 125 mm if the entire length of the second needle part 42 of the suture grasping needle 4 is equal to or larger than 80 mm and equal to or smaller than 100 mm.

If the length is within the above-stated range, the annular portion 53 is completely protruded from the opening of the suture grasping needle 4 when the handle portion 51 of the suture traction tool 5 is fitted into the second hub 41 of the suture grasping needle 4.

The annular portion 53 is deformed and almost linear in the suture grasping needle 4, and is annular in a state of protruding from the suture grasping needle 4. This can facilitate grasping the suture. It is, therefore, preferable that a material forming the annular portion 53 is elastic.

As shown in FIGS. 1 and 2, the annular portion 53 is formed so that a central axis of the suture insertion needle 3 or an extension thereof penetrates through an interior of the annular portion 53 in the state of protruding from the suture grasping needle 4. This can ensure grasping the suture.

A diameter of the annular portion 53 is not limited to a specific one. It is preferable that the diameter of the annular portion 53 is equal to or larger than 1.5 L and equal to or smaller than 3.0 L (mm) if it is assumed that the distance between the suture insertion needle 3 and the suture grasping needle 4 is L (mm). If the diameter is within the above-stated range, the annular portion 53 is particularly excellent in grasping the suture.

Although a wire diameter of the annular portion 53 is not limited to a specific one, it is preferably equal to or larger than 0.1 mm and equal to or smaller than 0.3 mm, more preferably equal to or larger than 0.14 mm and equal to or smaller than 0.24 mm. If the wire diameter is within the above-stated range, the annular portion can be kept annular even when a quite highly viscous matter, such as a stomach fluid, adheres.

A material constituting the rod portion 52 and the annular portion 53 is not limited to a specific one as long as the material is hard and elastically deformable. Examples of the material include metals such as stainless steel, and the rod portion 52 and the annular portion 53 are formed by metal working.

One embodiment of a method of using the medical device 1 according to the present invention will next be described based on FIGS. 8 to 16.

Figure 8:
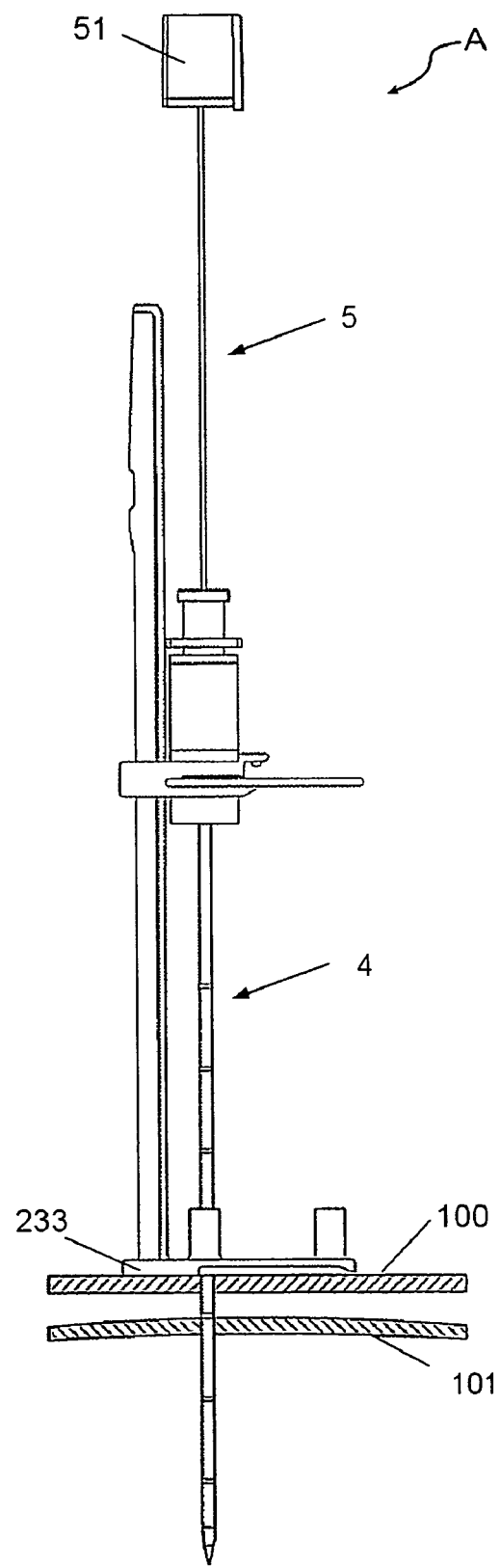
FIG. 8 is a front view showing a state of piercing the suture grasping needle from an abdominal wall through a gastric wall.

An internal organ fixing method of fixing an internal organ of a living body to a body surface using the medical device 1 according to the embodiment starts with slidably moving the first puncture needle 4, from which the second puncture needle 3 is separated, downward of the main body 2 and piercing the first puncture needle 4 from the body surface of the living body into the internal organ as shown in FIG. 8.

At this time, since the first puncture needle 4 has, for example, scale marks put on an outer circumferential surface, a piercing depth can be checked at a glance. Since the storage unit 23 is made of transparent and colorless resin, in particular, the marks of the first puncture needle 4 can be visually recognized even through the first storage portion 231.

Next, as shown in FIG. 9, the suture traction tool 5 is slidably moved downward within the first puncture needle 4 to protrude the annular portion 53 from the needlepoint downward of the second guide hole. The storage unit 23 as well as the main body 2 is rotated about the pierced first puncture needle 4 up to a desired position if it is necessary to do so, and the first puncture needle 4 is inclined with respect to the body surface up to a desired angle if it is necessary to do so.

As shown in FIG. 10, the second puncture needle 3 is inserted into the second guide hole of the storage unit 23 arranged at the desired position and pierced from the body surface into the internal organ, thereby opposing the lower end of the second puncture needle 3 to the annular portion 53.

Figure 11:
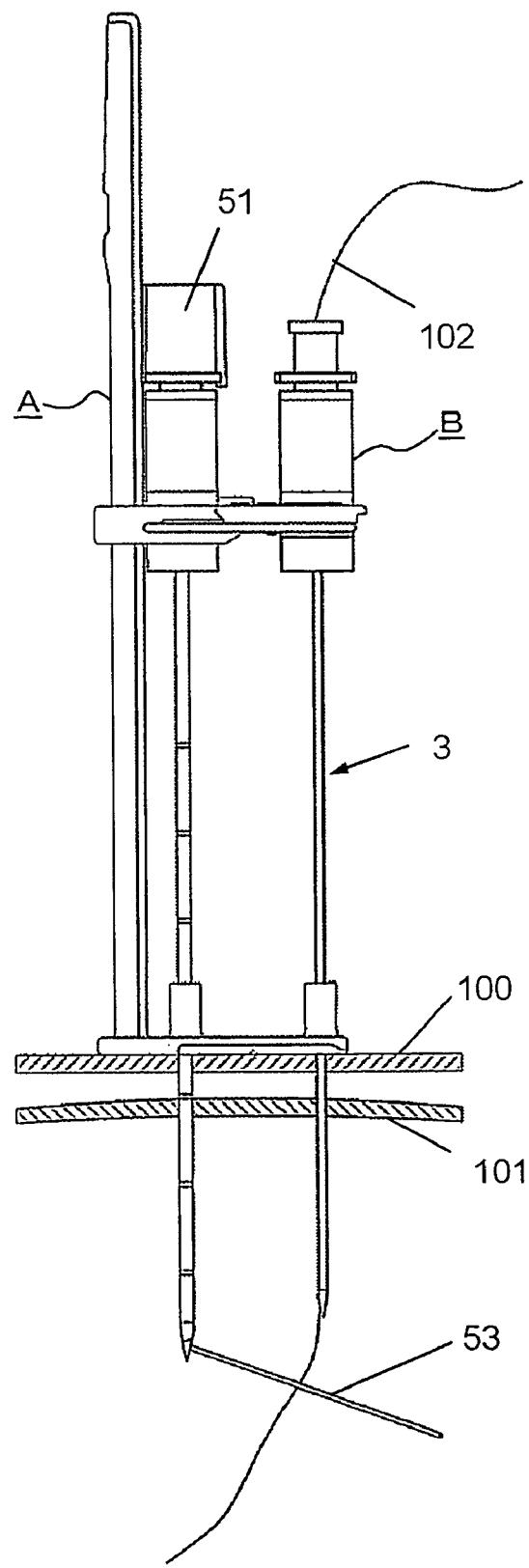
FIG. 11 is a front view showing a state of inserting a suture from the suture insertion needle.
Figure 12:
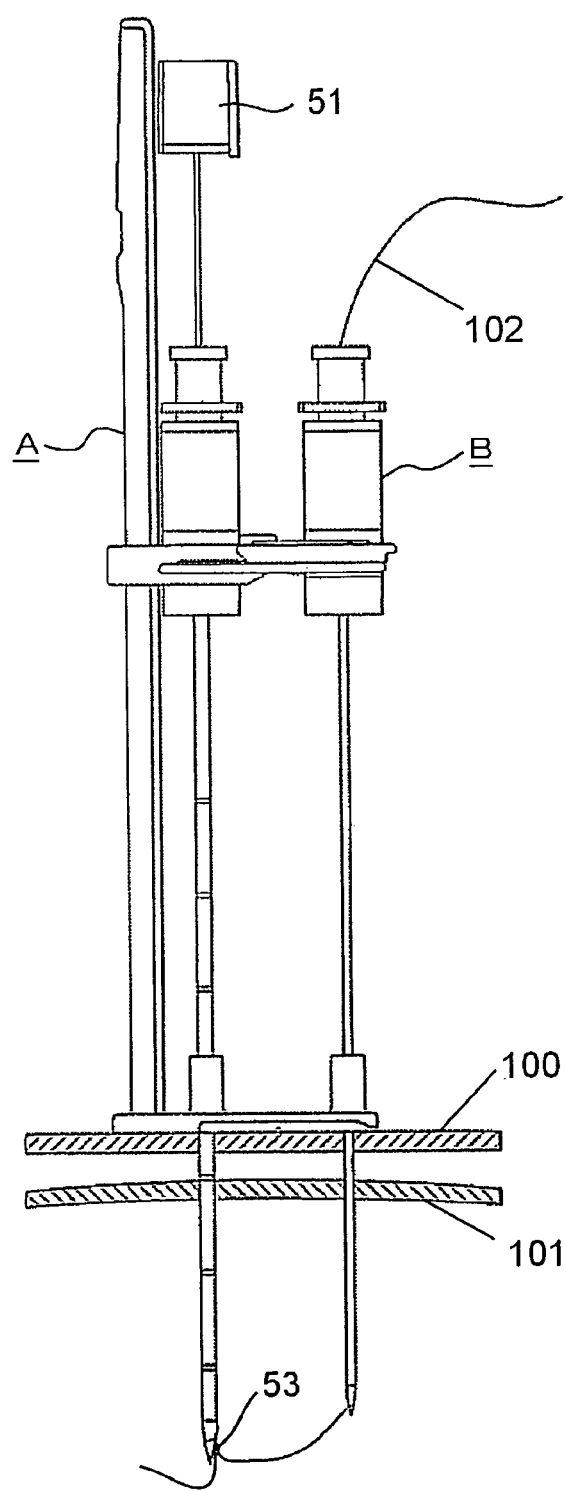
FIG. 12 is a front view showing a state of grasping the suture by the suture traction tool.

As shown in FIG. 11, a suture 102 is inserted into the second puncture needle 3 from the upper end thereof to protrude from the lower end thereof. As shown in FIG. 12, the suture traction tool 5 is slidably moved upward to allow the annular portion 53 to grasp the suture 102.

Figure 13:
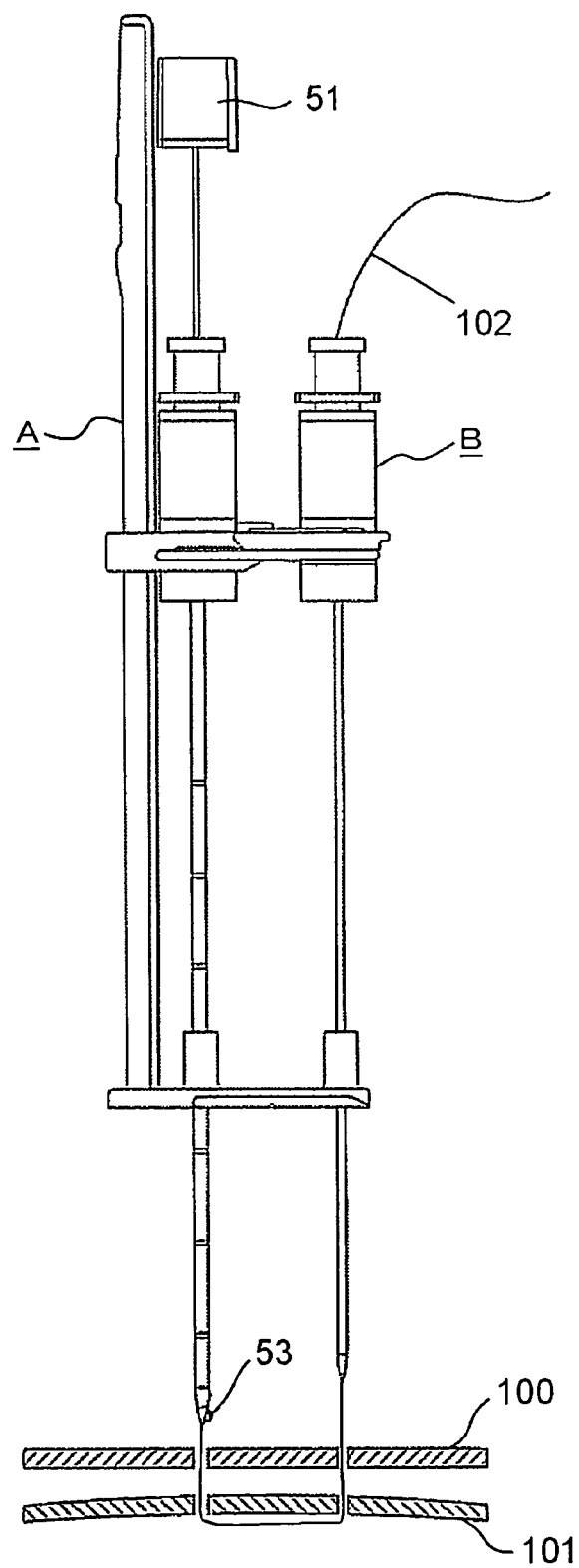
FIG. 13 is a front view showing a state of pulling out the main body from a patient.
Figure 14:
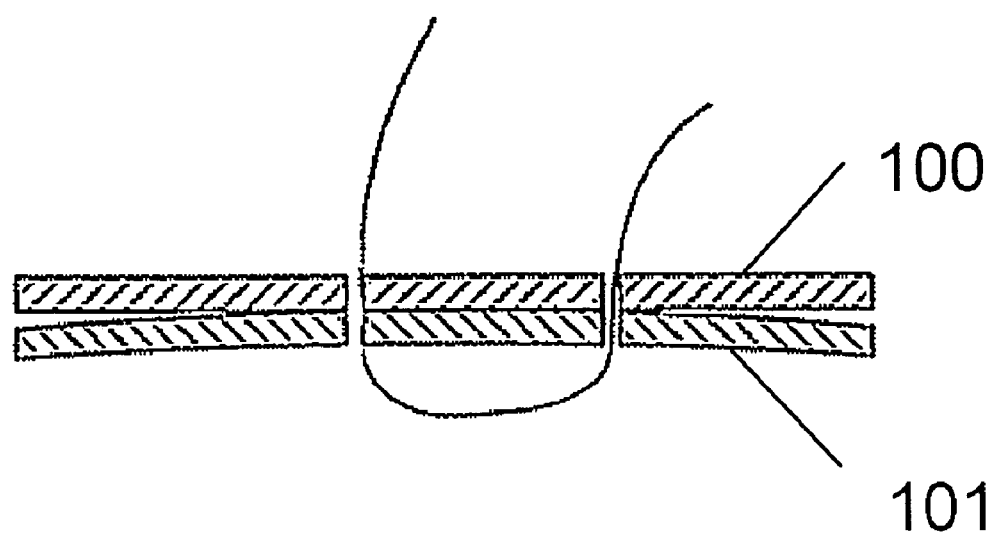
FIG. 14 is a front view showing a state in which both ends of the suture are exposed to a body surface from an interior of an internal organ.

In such a state, the medical device 1 is entirely pulled upward to remove the first and second puncture needles 4 and 3 from the living body as shown in FIG. 13. As a result, one end of the suture 102 grasped by the annular portion 53 of the suture traction tool 5 is exposed upward of the body surface as shown in FIG. 14. Therefore, by binding one end of the suture 102 to the other end, the internal organ can be fixed.

It is to be noted that rotation of the storage unit 23 just before piercing the second puncture needle 3 as stated above is executed up to a position at which the second puncture needle 3 is pierced through an outer surface of the internal organ almost at right angle. Likewise, inclination of the first puncture needle 4 just before piercing the second puncture needle 3 is executed up to an angle at which the second puncture needle 3 is pierced through the outer surface of the internal organ almost at right angle.

Figure 22:
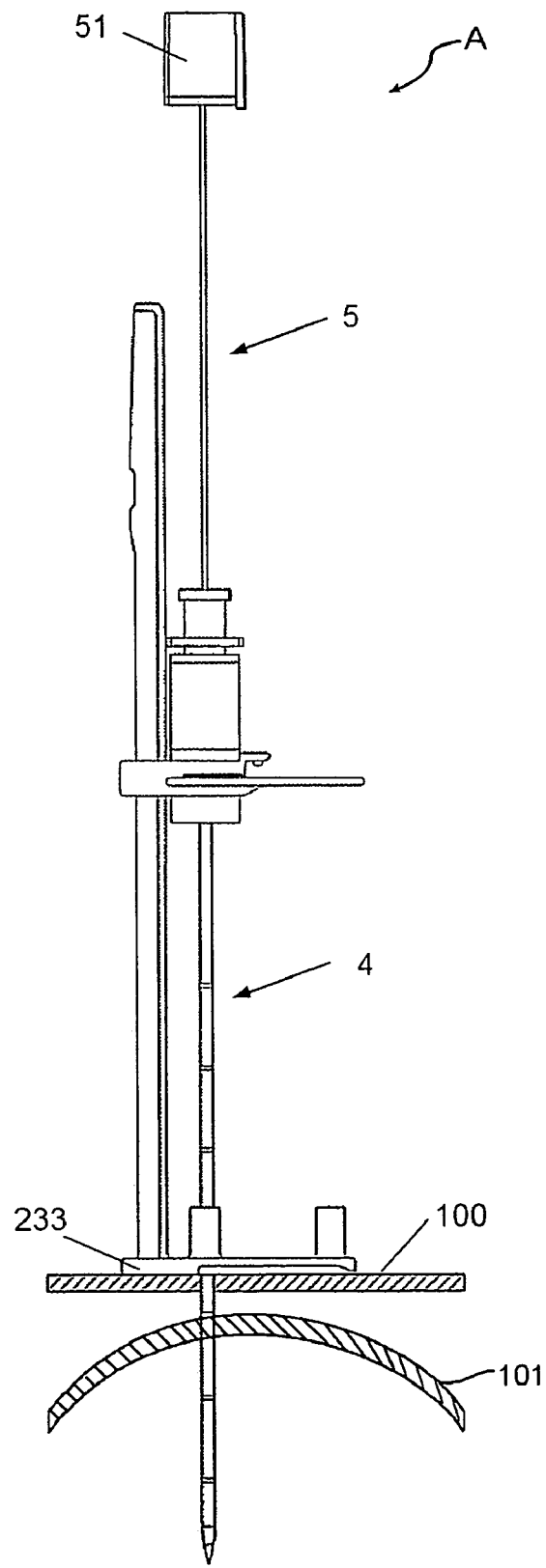
FIG. 22 is a typical front view showing a state of piercing the suture grasping needle from the abdominal wall through the gastric wall.
Figure 23:
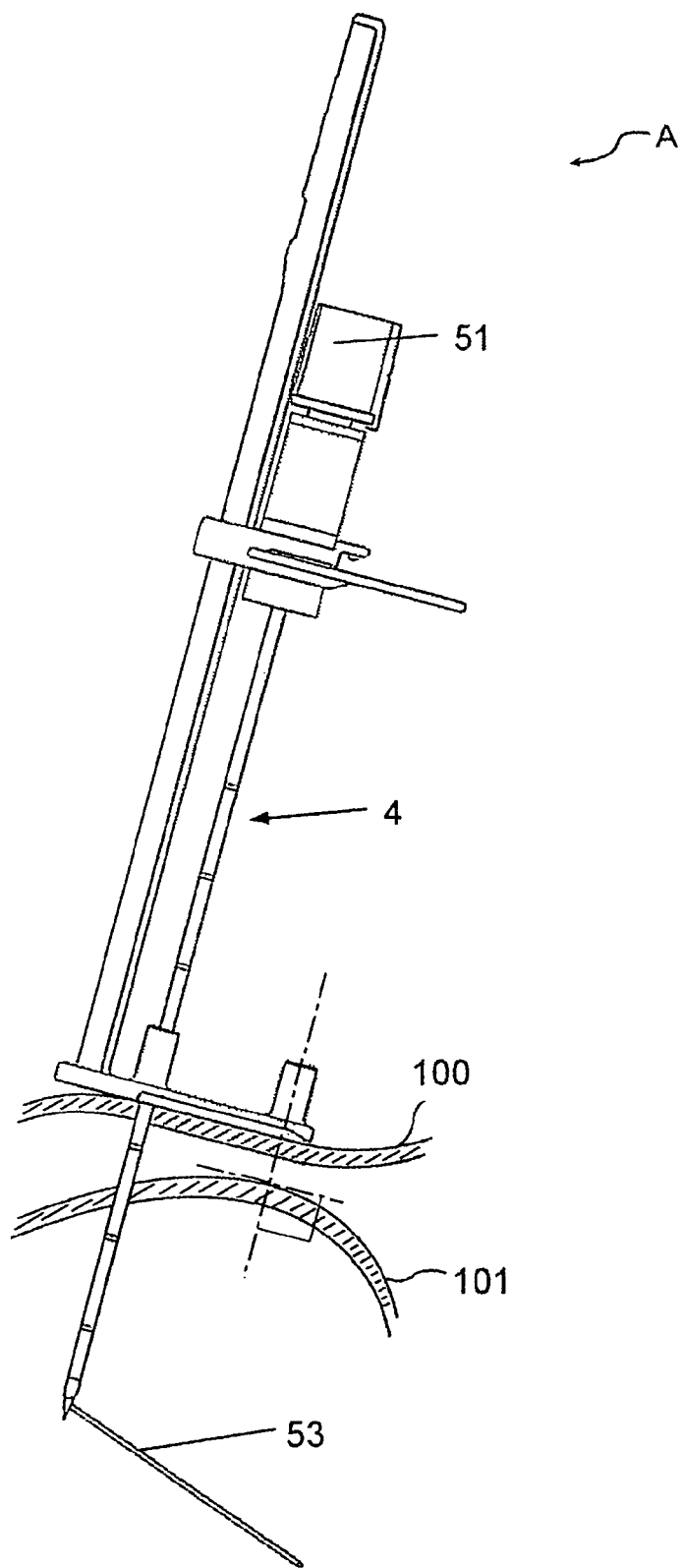
FIG. 23 is a typical front view showing a state of inclining the suture grasping needle.
Figure 24:
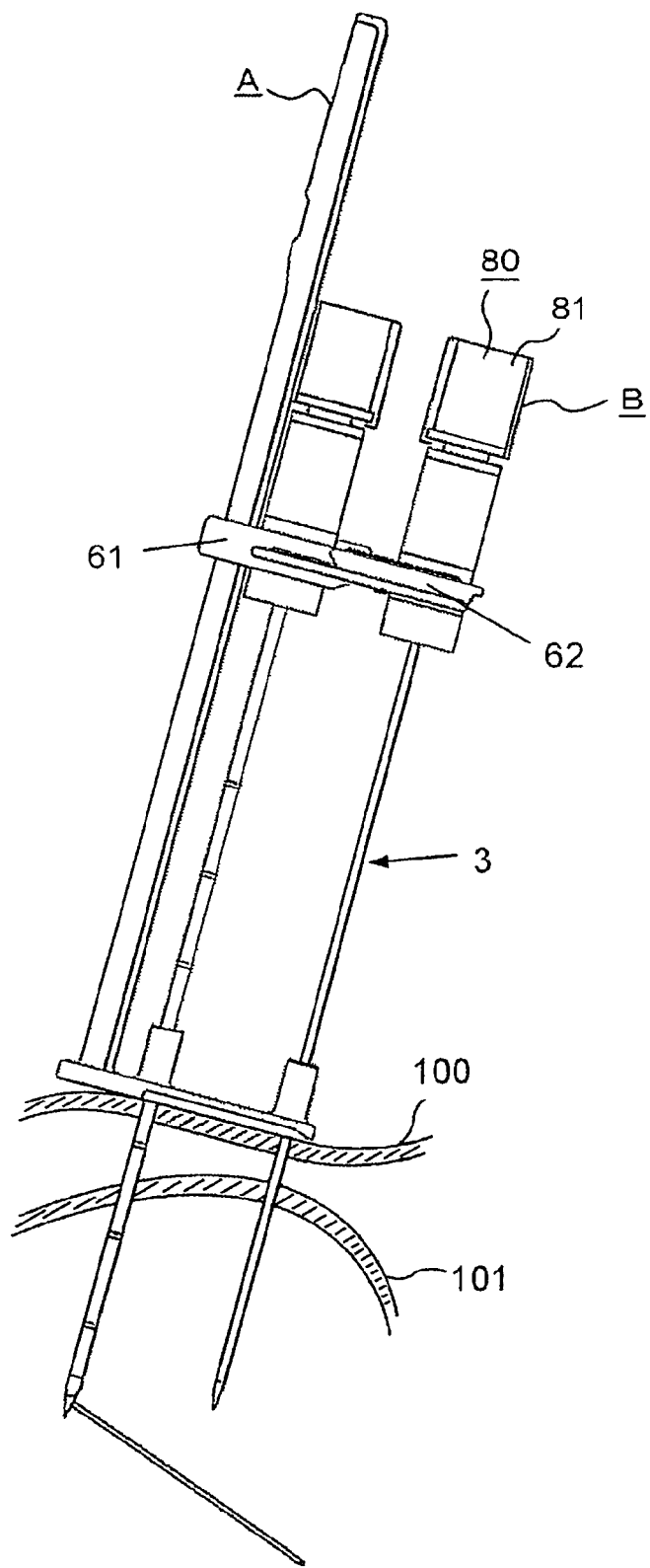
FIG. 24 is a typical front view showing a state of piercing the suture insertion needle while keeping the suture grasping needle inclined.

Namely, the internal organ into which the first puncture needle 4 and the second puncture needle 3 are pierced is a stomach or the like, and the outer surface of the internal organ is normally spherically curved as shown in FIG. 22. Due to this, if a piercing direction is set at almost right angle with respect to the outer surface of the internal organ as shown in FIG. 23, the second puncture needle 3 is smoothly pierced into the internal organ as shown in FIG. 24.

An endoscope (not shown) is inserted into the internal organ into which the first and second puncture needles 4 and 3 are pierced as stated in advance. An inner surface of the internal organ is observed near the position at which the first puncture needle 4 is pierced by the endoscope, whereby the storage unit 23 is rotated and the first puncture needle 4 is inclined so as to pierce the second puncture needle 3 into the outer surface of the internal organ almost at right angle.

More specifically, first, the endoscope is inserted into the stomach of a patient who is the living body before use of the medical device 1, the air is sufficiently fed, and an abdominal wall 100 is closely attached to a gastric wall 101. Next, a position of the stomach that is the internal organ is confirmed by a transmitted light from the endoscope, and an abdominal skin that is the body surface is disinfected and given a local anesthetic. A small incision is made in a relevant region by a scalpel. Depending on situations, the small incision region is broadened by a metal Pean forceps (not shown).

An abutment portion 233 of the main body 2 abuts on the abdominal wall 100 and the suture grasping needle 4 is pierced into the abdominal wall 100 and the gastric wall 101 of the patients almost at right angle from the small incision region (FIG. 8). At this time, even if the annular portion 53 of the suture traction tool 5 is stored in the internal cavity 43 of the suture grasping needle 4, the suture traction tool 5 may be detached.

The handle portion 51 of the suture traction tool 5 is operated to insert the suture traction tool 5 into the internal cavity 43 of the suture grasping needle 4 until a lower end of the handle portion 51 abuts on the hub 41. The annular portion 53 of the suture traction tool 5 thereby protrudes from the needlepoint of the suture grasping needle 4 and widens annularly (FIG. 9).

Next, the suture insertion needle 3 is pierced into the abdominal wall 100 and the gastric wall 101 of the patient almost perpendicularly through the second storage portion 232, and the second holding plate 62 holding the suture insertion needle 3 is mounted on the first holding plate 61. By mounting the second holding plate 62 on the first holding plate 61 so as to form an elliptic shape by the first and second holding plates, directions of the sharp needlepoints of the suture insertion needle 3 and the suture grasping needle 4 are set almost constant (FIG. 10).

As stated above, the medical doctor can decide the piercing position before piercing the suture insertion needle 3, and the support member 21 of the main body 2 is rotated about the suture grasping needle 4 to position the second storage portion 232 at the piercing position. Further, the first puncture needle 4 is inclined with respect to the body surface at up to the desired angle if it is necessary to do so.

In that case, the storage unit 23 is rotated and the first puncture needle 4 is inclined so as to observe the inner surface of the internal organ near the position at which the first puncture needle 4 is pierced by the endoscope and so that the second puncture needle 3 is pierced into the outer surface of the internal organ almost at right angle as stated above.

Moreover, the internal needle 80 is inserted into the suture insertion needle 3 as shown in FIG. 10 when piercing the suture insertion needle 3 as stated, whereby the inclined surface of the needlepoint of the internal needle 80 can be made flush with the inclined surface of the needlepoint of the second puncture needle 3 and the piercing resistance can be reduced, accordingly.

If the suture insertion needle 3 is appropriately pierced into up to the interior of the internal organ as stated, then the suture 102 is inserted into the internal cavity from the upper end of the suture insertion needle 3 and protruded from the needlepoint of the suture insertion needle 3. The suture 102 is thereby passed through the interior of the annular portion 53 of the suture traction tool 5 (FIG. 11).

Next, the suture traction tool 5 is pulled up toward the base end side (upper side in FIG. 11) with respect to the suture grasping needle 4, and the suture 102 is grasped by the annular portion 53 as shown in FIG. 12. In such a state, the medical device 1 is entirely pulled upward to remove the first and second puncture needles 4 and 3 from the living body as show in FIG. 13.

As a result, as shown in FIG. 14, the suture 102 inserted from the portion into which the suture insertion needle 3 is inserted passes from the abdominal wall 100 into the gastric wall 101 and turns into a state of protruding from the position at which the suture grasping needle 4 is pierced by these operation procedures. Therefore, the ends of the suture 102 are bound together to fix the abdominal wall 100 to the gastric wall 101.

After securing the abdominal wall 100 to the gastric wall 101 by the suture, the second holding plate 62 is forced into the first holding plate 61 side (support member 21 side of the main body 2). The convex portion provided in the first holding plate 61 is thereby fitted into the concave portion provided in the second holding plate 62, whereby the state turns into a state in which the first and second holding plates are fitted into each other.

At this time, the suture insertion needle 3 is not in a state of being parallel to the suture grasping needle 4 and the support member 21 but in a state of widening toward the end with respect to the suture grasping needle 4 and the support member 21 (FIG. 15). Due to this, it is possible to visually confirm that the suture insertion needle 3 has been used.

The operating unit 214 of the support member 21 of the main body 2 is forced into the tip end side (FIG. 16), the state is changed over to the state in which the sharp needlepoints of the suture grasping needle 4 and the suture insertion needle 3 are stored in the first storage portion 231 and the second storage portion 232 of the storage unit 23, respectively, and the medical device 1 is disposed of.

Since the above-stated operation enables the state of storing the needlepoints to be maintained, the secondary accident of erroneous piercing of the needles into healthcare professionals after disposal can be prevented. For example, the medical device of the Patent Document 1 stated above is disposed of while the needlepoints protrude after use, so that the secondary accident of erroneous piercing of the needles into healthcare professionals may possibly occur.

As stated so far, by using the medical device 1 according to the present invention, the sharp needlepoints of the two puncture needles can be completely covered with the main body during disposal of the medical device after finishing securing the abdominal wall 100 to the gastric wall 101 by the suture. Therefore, the medical device 1 can be disposed of safely. In addition, since it is possible to visually confirm that the medical device 1 has been used, the secondary accidents of erroneous piercing of the needles into healthcare professionals can be reduced.

Besides, the medical device 1 according to the embodiment is configured so that the first unit A including the main body 2, the first puncture needle 4, and the first holding plate 61 and the second unit B including the second puncture needle 3 and the second holding plate 62 are formed separately to be engageable with and disengageable from each other.

Due to this, the second puncture needle 3 can be pierced into the living body after piercing the first puncture needle 4 into the living body. Therefore, there is no need to simultaneously pierce the two puncture needles 3 and 4, and the piercing position of the second puncture needle 3 can be adjusted based on the piercing position of the first puncture needle 4, accordingly.

Moreover, after the first puncture needle 4 is pierced, the second puncture needle 3 can be pierced while being inclined at the desired angle. Due to this, as shown in FIGS. 22 to 24, even if the outer surface of the internal organ is spherically curved, the second puncture needle 3 can be pierced into the internal organ at right angle. It is, therefore, possible to prevent the second puncture needle 3 from failing to be smoothly pierced into the spherically curved outer surface of the internal organ and the outer surface of the internal organ from being damaged.

Further, the inner surface of the internal organ near the position at which the first puncture needle 4 is pierced can be observed by the endoscope. Generally, inner and outer surfaces of an internal organ are almost parallel. Due to this, it is easy to rotate the storage unit 23 and incline the first puncture needle 4 so that the second puncture needle 3 is pierced into the outer surface of the internal organ almost at right angle.

Moreover, in the medical device 1 according to the embodiment, the second holding plate 62 of the second puncture needle 3 abuts on the first holding plate 61 of the first puncture needle 4 from above in an approachable and separable manner. Due to this, while the second puncture needle 3 is pierced separately from the first puncture needle 4, the needlepoint of the second puncture needle 3 is automatically arranged at a position opposed to the needlepoint of the first puncture needle 4.

Therefore, despite the structure of separately piercing the two puncture needles 3 and 4 as stated above, the annular portion 53 of the suture traction tool 5 protruding from the lower end of the first puncture needle 4 can easily and surely grasp the suture 102 protruding from the lower end of the second puncture needle 3.

Furthermore, in the medical device 1 according to the embodiment, the upper end distance between the first and second puncture needles 4 and 3 is smaller than the distance between the first and second guide holes of the storage unit 23 in the state in which the first and second holding plates 61 and 62 are connected to each other by the convex portion 611 and the concave portion 621.

Due to this, in the state in which the first and second holding plates 61 and 62 are connected, it is difficult to smoothly slidably move the first and second puncture needles 4 and 3. It is, therefore, possible to satisfactorily prevent the erroneous operation of simultaneously piercing the first and second puncture needles 4 and 3 into the living body while the first and second holding plates 61 and 62 are kept connected.

If the first and second puncture needles 4 and 3 are pierced into the living body while the first and second holding plates 61 and 62 are kept connected, the first and second puncture needles 4 and 3 are pierced into the living body while widening toward the ends.

It is difficult to remove the first and second puncture needles 4 and 3 pierced while widening toward the ends from the living body as they are. If they are forcibly removed, then the living body may possibly be damaged and a severe pain may possibly be inflicted on the patient.

A defect that the needlepoints of the first and second puncture needles 4 and 3 widen in the interior of the living body by the above-stated erroneous operation is more conspicuous if the distance from the body surface to the internal organ is longer by, for example, thick subcutaneous fat of the patient.

Furthermore, if the first and second puncture needles 4 and 3 are widen as stated above, it is also difficult for the annular portion 53 of the suture traction tool 5 to grasp the suture 102 protruding from the needlepoint of the second puncture needle 3.

Moreover, the outer surface of the internal organ such as the stomach into which the first and second puncture needles 4 and 3 are pierced is spherically curved as stated above. Due to this, if the first and second puncture needles 4 and 3 are simultaneously pierced so as to widen toward the ends, one of the needles 4 and 3 may possibly fail to be smoothly pierced into the internal organ, resulting in damage on the outer surface of the internal organ.

Accordingly, with the medical device 1 according to the embodiment, to pierce the first and second puncture needles 4 and 3 into the living body while the first and second holding plate 61 and 62 are connected cannot be carried out as a medical treatment.

On the other hand, in the state in which the first and second holding plates 61 and 62 the convex portion 611 and the concave portion 621 of which are disconnected are engaged, the upper end distance between the first and second puncture needles 4 and 3 is larger than the distance between the first and second guide holes of the storage unit 23.

Due to this, it is also difficult to smoothly slidably move the first and second puncture needles 4 and 3 while the first and second holding plates 61 and 62 are kept engaged. It is, therefore, possible to satisfactorily prevent the erroneous operation of simultaneous piercing of the first and second puncture needles 4 and 3 into the living body even in the state in which the first and second holding plates 61 and 62 are engaged without being connected to each other.

If the first and second puncture needles 4 and 3 are pierced into the living body in the state in which the first and second holding plates 61 and 62 which are disconnected from each other are engaged, the needlepoints of the first and second puncture needles 4 and 3 are closer to each other in the interior of the living body into a tapered shape.

It is similarly difficult to remove first and second puncture needles 4 and 3 pieced while widening in the tapered fashion from the living body as they are. If they are forcibly removed, the living body may possibly be similarly damaged. Due to this, the first and second puncture needles 4 and 3 cannot be pierced into the living body while the first and second holding plates 61 and 62 are engaged.

Namely, the medical device 1 according to the embodiment is formed to have the structure for piercing the first puncture needle 4 and the second puncture needle 3 in order as stated above and formed to have the structure prohibiting the first puncture needle 4 and the second puncture needle 3 from being simultaneously pierced.

Moreover, since the first puncture needle 4 is formed as the Huber needle, the annular portion 53 of the suture traction tool 5 can be easily protruded from the opening of the needlepoint of the first puncture needle 4 in the appropriate direction. Particularly by engaging the handle portion 51 of the suture traction tool 5 with the first puncture needle 4, it is possible to ensure protruding the annular portion 53 from the opening of the needlepoint in the appropriate direction.

It is to be noted, however, that the first puncture needle 4 constituted by the Huber needle is higher in piercing resistance than the second puncture needle 3 the needlepoint of which has the inclined surface. Nevertheless, with the medical device 1 according to the embodiment, the first and second puncture needles 4 and 3 are not simultaneously pierced as stated above. Due to this, the piercing resistance of the first puncture needle 4 constituted by the Huber needle does not produce any problem.

Moreover, as stated above, if the suture insertion needle 3 is to be pierced, the internal needle 80 is inserted into the suture insertion needle 3 as shown in FIG. 10. It is thereby possible to make the inclined surfaces of the needlepoints of the internal needle 80 and the second puncture needle 3 flush with each other and to reduce the piercing resistance.

Besides, the second puncture needle 3 having the hollow structure can be supported from inward by the internal needle 80. This can prevent bending or the like of the pierced second puncture needle 3. It is also possible to prevent tissues from entering the interior of the suture insertion needle 3 pierced into the living body to make it difficult to insert the suture 102.

Moreover, with the medical device 1 according to the embodiment, the handle portion 81 of the internal needle 80 is engaged with the upper end of the second puncture needle 3, whereby the inclined surfaces of the needlepoints of the internal needle 80 and the second puncture needle 3 can be made flush with each other easily and surely.

Additionally, in the medical device 1 according to the embodiment, the main body 2 includes the locking part 212 locking the first puncture needle 4 while the needlepoint is being stored in the first storage portion 231, and the needlepoint of the second puncture needle 3 connected to the locked first puncture needle 4 by the convex portion 611 and the concave portion 621 is stored in the second storage portion 232.

This can prevent the sharp needlepoints of the first and second puncture needles 4 and 3, of the used medical device 1 from being exposed. Therefore, the medical device 1 can be safely disposed of with the simple structure.

Moreover, in the medical device 1 according to the embodiment, the function of restricting the sliding directions of the first and second puncture needles 4 and 3 and the function of storing the sharp lower ends of the first and second puncture needles 4 and 3 are shared between the cylindrical first and second storage portions 231 and 232.

It is, therefore, possible to restrict the sliding directions of the first and second puncture needles 4 and 3 and to store the sharp lower ends thereof with the simple and practical structure, and easily and quickly change over between the sliding state and the storage state.

While the medical device according to the present invention has been described so far based on the embodiment, the present invention is not limited to the embodiment. For example, shapes of the support unit, the abutment portion, and the like of the main body, shapes and the like of the hubs of the suture insertion needle and the suture grasping needle may differ from those according to the above-stated embodiment.

For example, another embodiment will be described with reference to FIG. 17. A medical device according to another embodiment is almost identical to that according to the preceding embodiment. However, differently from the preceding embodiment, in the medical device according to another embodiment configured so that the first claw 71 is present on the first holding plate 61 and so that the second claw 72 is present on the second holding plate 62, the second holding plate 62 is forced into the first holding plate 61 side (support member 21 side of the main body 2) after use, whereby the second claw 72 provided on the second holding plate 62 overrides the first claw 71 provided on the first holding plate 61 and the first holding plate 61 is engaged with the second holding plate 62. Further, the operating unit 214 of the main body 2 is forced into the tip end side while the tip end side of the first holding plate 61 is held by the hand, whereby sharp needlepoints of the two puncture needles are stored in the storage unit 23.

Moreover, as shown in FIGS. 12 and 13, the above-stated embodiment exemplarily shows that the annular portion 53 of the suture traction tool 5 grasps the suture 102 within the internal organ into which the first and second puncture needles 4 and 3 are pierced, and that the medical device 1 in this state is entirely pulled upward to remove the first and second puncture needles 4 and 3 from the living body. By doing so, as shown in FIG. 14, the state is turned into the state in which both ends of the suture 102 protrude from the interior of the internal organ toward the body surface.

Alternatively, the medical device 1 can be used for an internal organ fixing method other than the above-stated method. The other internal organ fixing method will be described below. First, similarly to the above-stated method, the annular portion 53 of the suture traction tool 5 grasps the suture 102 within the internal organ into which the first and second puncture needles 4 and 3 are pierced.

Next, the suture traction tool 5 is further pulled up toward the base end side and the suture traction tool 5 grasping the suture 102 is completely pulled out from the suture grasping needle 4.

Figure 19:
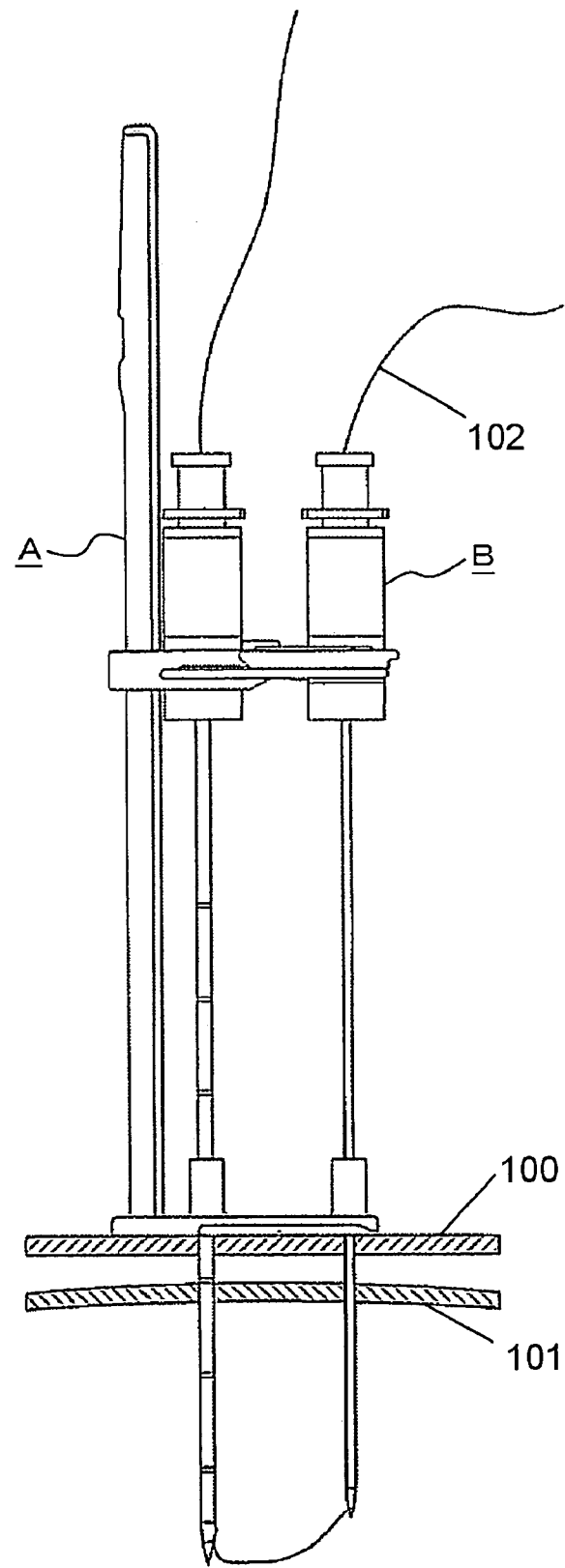
FIG. 19 is a front view showing a state of pulling the suture grasped by the suture traction tool up to the body surface.

By doing so, a state in which one end of the suture 102 passes from the body surface part through an interior of the gastric wall 101 via the suture insertion needle 3 and the suture grasping needle 4 and then protrudes to the body surface part can be realized as shown in FIG. 19.

Figure 20:
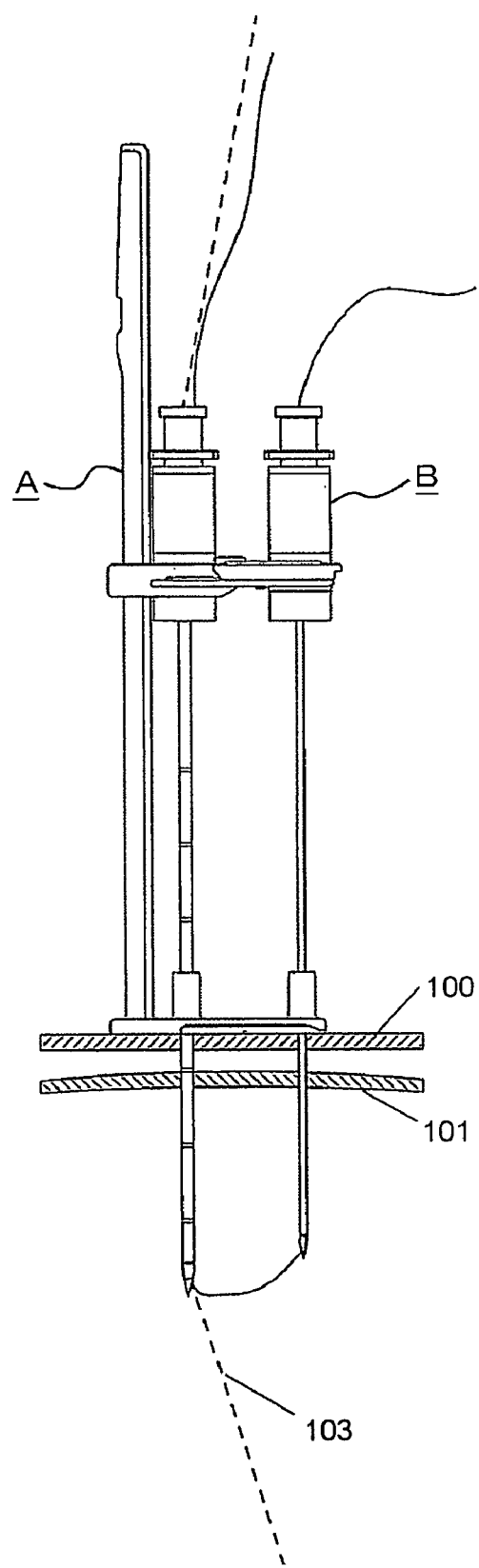
FIG. 20 is a front view showing a state of inserting a storage wire.

Next, as shown in FIG. 20, a storage wire 103 is inserted from the second hub 41 of the suture grasping needle 4. Thereafter, the main body 2 is pulled out from the abdominal part 100.

Figure 21:
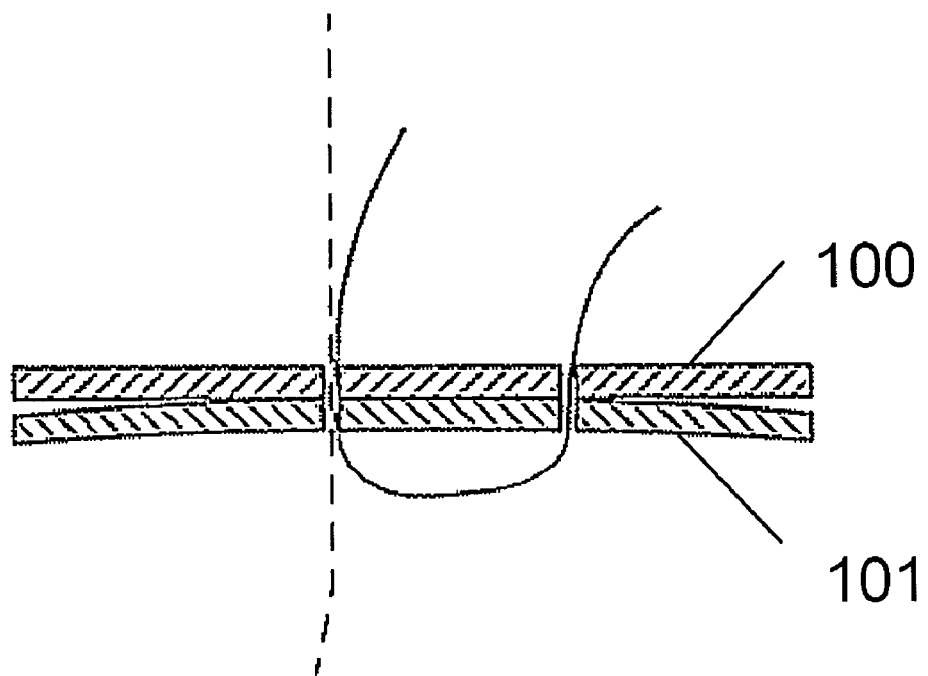
FIG. 21 is a front view showing a state of pulling out the main body from the patient.

As shown in FIG. 21, these operation procedures turn the state into a state in which the suture 102 inserted from the portion into which the suture insertion needle 3 is inserted passes from the abdominal wall 100 through the interior of the gastric wall 101 and protrudes from the position at which the suture grasping needle 4 is pierced.

Moreover, the state is turned into a state in which the storage wire 103 is inserted into up to the interior of the gastric wall 101 at the position at which the suture grasping needle 4 is pierced. By binding ends of the suture 102 together, the abdominal wall 100 can be fixed to the gastric wall 101.

Furthermore, the above-stated embodiment exemplarily shows that the handle portion 51 of the suture traction tool 5 is engaged with the upper end of the first puncture needle 4, whereby the annular portion 53 of the suture traction tool 5 protrudes from the opening of the needlepoint of the first puncture needle 4 constituted by the Huber needle in the appropriate direction. Alternatively, a mark indicating the direction of the suture traction tool 5 may be formed on an upper surface of the handle portion 51.

Likewise, the above-stated embodiment exemplarily shows that the inclined surfaces of the needlepoints of the second puncture needle 3 and the internal needle 80 are made flush with each other by engaging the handle portion 81 of the internal needle 80 with the upper end of the second puncture needle 3. Alternatively, a mark indicating the direction of the internal needle 80 may be formed on the upper surface of the handle portion 81.

Furthermore, regions of the living body in which the medical device is used are not limited to the abdominal wall and the gastric wall but the medical device can be used for lifting of a wall of each internal organ, a blood vessel, a nerve or the like up to the abdominal wall or the like. Moreover, the above-stated embodiment exemplarily shows fixing of the internal organ of the human body. Alternatively, the present invention may be applied to living bodies other than the human body.

The invention claimed is:

1. A medical device comprising:
a first unit including
   a main body elongated in a vertical direction;
   a guide unit through which a first guide hole and a second guide hole are penetrated in the vertical direction, the guide unit protruding from a lower end of said main body in a direction orthogonal to said vertical direction;
   a first puncture needle of a hollow structure supported by said main body slidably in the vertical direction, and having a sharp lower end slidably inserted into said first guide hole from above; and
   a first holding plate integrally fixed to said first puncture needle; and
a second unit including
   a second puncture needle of a hollow structure, having a sharp lower end slidably inserted into said second guide hole from above; and
   a second holding plate integrally fixed to said second puncture needle, wherein
said first unit and said second unit are formed separately to be engageable with and disengageable from each other,
said second holding plate of said second puncture needle inserted into said second guide hole approachably and separably abuts on said first holding plate of said first puncture needle from above,
said guide unit has a first storage portion provided with said first guide hole and a second storage portion provided with said second guide hole,
said first holding plate and said second holding plate include connectors approachably and separably connected to each other respectively,
said main body includes a locking part locking said first puncture needle in a state in which a needlepoint of said first puncture needle is stored in said first storage portion, and wherein in a state in which said first holding plate is connected to said second holding plate on said connectors, provided that said locking part is locking said first puncture needle:
  (i) an upper end distance between said first puncture needle and said second puncture needle becomes smaller than a distance between said first guide hole and said second guide hole so that said second puncture needle is not in a state parallel to said first puncture needle but in a state of widening toward the lower end with respect to said first puncture needle, and
  (ii) a needlepoint of said second puncture needle is stored in said second storage portion.

2. The medical device as claimed in claim 1,
wherein said first storage portion and said second storage portion are cylindrical.

3. The medical device as claimed in claim 1,
wherein a slide hole in which said main body is slidably located is formed in said first holding plate, and
said locking part is formed on said main body as a concave portion with which said first holding plate sliding in said slide hole is detachably engaged.

4. The medical device as claimed in claim 1, further comprising:
  a suture traction tool including
    a rod portion slidably arranged within said first puncture needle;
    a handle portion formed integrally with an upper end of said rod portion, and
  located upward of the upper end of said first puncture needle; and
    an annular portion formed integrally with a lower end of said rod portion, and
  protruding and retreating from the lower end of said first puncture needle.

5. A medical device comprising:
a main body;
a first holding plate provided slidably with respect to said main body;
a first puncture needle held by said first holding plate;
a second holding plate detachably and movably mounted on said first holding plate; and
a second puncture needle held by said second holding plate,
wherein an engagement unit engaging said second holding plate with said first holding plate is provided in a state in which said second puncture needle is moved to approach said first puncture needle,
wherein a base end side of said main body includes a locking part locking said first holding plate at a predetermined position,
wherein a storage portion storing needlepoints of said first puncture needle and said second puncture needle is provided on a tip end side of said main body, and
wherein in a state in which said first holding plate is caused to slide toward said base end side of said main body and locked by said locking part, provided that said first holding plate is engaged with said second holding plate by said engagement unit:
  (i) said second puncture needle is not in a state of being parallel to said first puncture needle but in a state of widening toward said lower end with respect to said first puncture needle, and
  (ii) said needlepoints of said first puncture needle and said second puncture needle are stored in said storage section.

6. The medical device as claimed in claim 5,
wherein said second holding plate is restricted from moving to said first holding plate in a predetermined direction.

7. The medical device as claimed in claim 5,
wherein said first and second puncture needles are mounted so that openings of needlepoints of said first and second puncture needles are opposed to each other.

8. The medical device as claimed in claim 5,
wherein said engagement unit is configured to include a concave portion provided in one of said first holding plate and said second holding plate and a convex portion provided in the other of said first and second holding plates.

9. The medical device as claimed in claim 5,
wherein said engagement unit is configured to include a first claw provided on said first holding plate and a second claw provided on said second holding plate.

10. The medical device as claimed in claim 5,
wherein an attitude of said second puncture needle with respect to said first puncture needle changes to a different attitude by moving said second holding plate toward said first holding plate.

11. The medical device as claimed in claim 5,
wherein said first or second holding plate includes a restriction unit restricting movement of said second holding plate holding said second puncture needle in a sliding direction.

12. The medical device as claimed in claim 11,
wherein said restriction unit is a member which is a projecting part of said first holding plate and which covers up a part of said second holding plate.

13. A method of fixing an internal organ of a living body to a body surface using the medical device as claimed in claim 4, comprising:
  slidably moving said first puncture needle downward with respect to said main body to pierce said first puncture needle from the body surface of said living body into said internal organ, said suture traction tool being inserted into said first puncture needle and said second puncture needle being separated from said first puncture needle;
  slidably moving said suture traction tool downward within said first puncture needle to protrude said annular portion downward of said second guide hole from a tip end of said first puncture needle;
  rotating said guide unit as well as said main body around said pierced first puncture needle up to a desired position according to need;
  inserting said second puncture needle into said second guide hole of said guide unit arranged at the desired position to pierce said second puncture needle into up to an interior of said internal organ, thereby opposing the lower end of said second puncture needle to said annular portion;
  inserting a suture into said second puncture needle from the upper end of said second puncture needle, and protruding the suture from the lower end of said second puncture needle;
  slidably moving said suture traction tool upward to cause said annular portion to grasp said suture; and
  exposing one end of said suture grasped by said annular portion to upward of said body surface, and binding the one end of said suture to other end of said suture.

14. The method of fixing the internal organ as claimed in claim 13, wherein said rotating said guide unit is executed up to a position at which said second puncture needle is pierced into an outer surface of said internal organ almost at right angle.

15. The method of fixing the internal organ as claimed in claim 14, comprising:
   inserting an endoscope into said internal organ; and
   observing an inner surface of said internal organ near a position at which said first puncture needle is pierced using said endoscope.

16. A method of fixing an internal organ of a living body to a body surface using the medical device as claimed in claim 4, comprising:
   slidably moving said first puncture needle downward with respect to said main body to pierce said first puncture needle from the body surface of said living body into said internal organ, said suture traction tool being inserted into said first puncture needle and said second puncture needle being separated from said first puncture needle;
   slidably moving said suture traction tool downward within said first puncture needle to protrude said annular portion downward of said second guide hole from a tip end of said first puncture needle;
   inclining said pierced first puncture needle with respect to said body surface at up to a desired angle according to need;
   inserting said second puncture needle into said second guide hole of said guide unit arranged at a desired position to pierce said second puncture needle into up to an interior of said internal organ, thereby opposing the lower end of said second puncture needle to said annular portion;
   inserting a suture into said second puncture needle from the upper end of said second puncture needle, and protruding the suture from the lower end of said second puncture needle;
   slidably moving said suture traction tool upward to cause said annular portion to grasp said suture;
   and exposing one end of said suture grasped by said annular portion to upward of said body surface, and binding the one end of said suture to other end of said suture.

17. The method of fixing the internal organ as claimed in claim 16,
   wherein said inclining said first puncture needle is executed up to an angle at which said second puncture needle is pierced into an outer surface of said internal organ almost at right angle.

18. The method of fixing the internal organ as claimed in claim 17, comprising:
   inserting an endoscope into said internal organ; and
   observing an inner surface of said internal organ near a position at which said first puncture needle is pierced using said endoscope.

19. The method of fixing the internal organ as claimed in claim 16,
   wherein the outer surface of said internal organ into which said first puncture needle and said second puncture needle are pierced is spherically curved.

20. A method of fixing an internal organ of a living body to a body surface using the medical device as claimed in claim 4, comprising:
   slidably moving said first puncture needle downward with respect to said main body to pierce said first puncture needle from the body surface of said living body into said internal organ, said suture traction tool being inserted into said first puncture needle and said second puncture needle being separated from said first puncture needle;
   slidably moving said suture traction tool downward within said first puncture needle to protrude said annular portion downward of said second guide hole from a tip end of said first puncture needle;
   rotating said guide unit as well as said main body around said pierced first puncture needle up to a desired position according to need, and inclining said first puncture needle with respect to said body surface at up to a desired angle according to need;
   inserting said second puncture needle into said second guide hole of said guide unit arranged at the desired position to pierce said second puncture needle into up to an interior of said internal organ, thereby opposing the lower end of said second puncture needle to said annular portion;
   inserting a suture into said second puncture needle from the upper end of said second puncture needle, and protruding the suture from the lower end of said second puncture needle;
   slidably moving said suture traction tool upward to cause said annular portion to grasp said suture; and
   exposing one end of said suture grasped by said annular portion to upward of said body surface, and binding the one end of said suture to other end of said suture.

21. The method of fixing the internal organ as claimed in claim 20,
   wherein said rotating said guide unit is executed up to a position at which said second puncture needle is pierced into an outer surface of said internal organ almost at right angle, and
   said inclining said first puncture needle is executed up to an angle at which said second puncture needle is pierced into the outer surface of said internal organ almost at right angle.

22. The method of fixing the internal organ as claimed in claim 21, comprising:
   inserting an endoscope into said internal organ; and
   observing an inner surface of said internal organ near a position at which said first puncture needle is pierced using the said endoscope.

23. The method of fixing the internal organ as claimed in claim 20,
   wherein the outer surface of said internal organ into which said first puncture needle and said second puncture needle are pierced is spherically curved.

24. A medical device comprising:
   a main body,
   a first holding plate, a first puncture needle held by said first holding plate and slidably supported by said main body, a second holding plate detachably and movably mounted on said first holding plate from above, a second puncture needle held by said second holding plate, wherein an edge face of said second holding plate facing toward said first holding plate slopes down and away from said first holding plate, such that said edge face is configured to be moveable to a position below said first holding plate in a state in which said second holding plate holding said second puncture needle abuts on said first holding plate holding said first puncture needle from above, and said medical device further comprising a restriction unit which covers up a part of said second holding plate so as to restrict movement of said second holding plate in sliding upward with respect to said first holding plate in a state in which said edge face is under said first holding plate.

* * * * *